(12) United States Patent
Kane et al.

(10) Patent No.: US 8,057,446 B2
(45) Date of Patent: Nov. 15, 2011

(54) WOUND HEALING DEVICE

(75) Inventors: Bartholomew J. Kane, Swarthmore, PA (US); Dennis P. Orgill, Belmont, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 537 days.

(21) Appl. No.: 12/112,527

(22) Filed: Apr. 30, 2008

(65) Prior Publication Data

US 2008/0275409 A1 Nov. 6, 2008

Related U.S. Application Data

(60) Provisional application No. 60/927,069, filed on May 1, 2007.

(51) Int. Cl.
*A61F 13/00* (2006.01)
(52) U.S. Cl. ........ 604/305; 604/304; 604/306; 604/307; 604/308; 604/311; 604/313; 604/315; 604/540; 604/543; 604/317
(58) Field of Classification Search .................. 604/304, 604/305–308, 311, 313, 315, 317, 540, 543
See application file for complete search history.

(56) References Cited

U.S. PATENT DOCUMENTS

| | | | |
|---|---|---|---|
| 4,044,404 A | 8/1977 | Martin et al. |
| 4,382,441 A | 5/1983 | Svedman |
| 4,587,101 A | 5/1986 | Marsoner et al. |
| 4,817,594 A | 4/1989 | Juhasz |
| 4,921,483 A | 5/1990 | Wijay et al. |
| 5,759,570 A | 6/1998 | Arnold |
| 5,833,641 A | 11/1998 | Curtis et al. |
| 5,876,432 A | 3/1999 | Lau et al. |
| 5,904,659 A | 5/1999 | Duarte et al. |
| 6,071,267 A | 6/2000 | Zamierowski |
| 6,282,444 B1 | 8/2001 | Kroll et al. |
| 6,420,622 B1 | 7/2002 | Johnston et al. |
| 6,436,129 B1 | 8/2002 | Sharkey et al. |
| 6,458,109 B1 | 10/2002 | Henley et al. |

(Continued)

FOREIGN PATENT DOCUMENTS

WO    WO 01/02093 A1    1/2001

(Continued)

OTHER PUBLICATIONS

Chung, S. et al., 2003, "Plastic microchip flow cytometer based on 2- and 3-dimensional hydrodynamic flow focusing," *Microsystem Technologies*, 9: 525-533.

(Continued)

*Primary Examiner* — Tatyana Zalukaeva
*Assistant Examiner* — Ginger T Chapman
(74) *Attorney, Agent, or Firm* — Wolf, Greenfield & Sacks, P.C.

(57) ABSTRACT

Methods and devices transmit micromechanical forces locally on the millimeter to micron scale for promoting wound healing. Micromechanical forces can selectively be applied directly to tissue, in some embodiments, by using microchambers fluidically connected to microchannels. Each chamber, or in some cases, group of chambers, may be associated with a valve to control vacuum pressure, positive pressure, liquid delivery, and/or liquid removal from each chamber or group of chambers. Application of embodiments of the invention may shorten wound-healing time, reduce costs of therapy, enable restoration of functional tissue, and reduce the need for more invasive therapies, including surgery.

18 Claims, 17 Drawing Sheets

U.S. PATENT DOCUMENTS

| | | |
|---|---|---|
| 6,479,072 B1 | 11/2002 | Morgan et al. |
| 6,514,515 B1 | 2/2003 | Williams |
| 6,553,998 B2 | 4/2003 | Heaton et al. |
| 6,613,082 B2 | 9/2003 | Yang |
| 6,632,656 B1 | 10/2003 | Thomas et al. |
| 6,685,681 B2 | 2/2004 | Lockwood et al. |
| 6,695,823 B1 | 2/2004 | Lina et al. |
| 6,695,824 B2 | 2/2004 | Howard et al. |
| 6,735,468 B2 | 5/2004 | Treppo et al. |
| 6,755,807 B2 | 6/2004 | Risk, Jr. et al. |
| 6,767,194 B2 | 7/2004 | Jeon et al. |
| 6,855,135 B2 | 2/2005 | Lockwood et al. |
| 6,867,342 B2 | 3/2005 | Johnston et al. |
| 6,899,873 B2 | 5/2005 | Ma et al. |
| 6,939,569 B1 | 9/2005 | Green et al. |
| 7,018,401 B1 | 3/2006 | Hyodoh et al. |
| 7,196,054 B1 | 3/2007 | Drohan et al. |
| 2001/0007658 A1 | 7/2001 | Usala et al. |
| 2002/0009805 A1 | 1/2002 | Nevo et al. |
| 2002/0068913 A1 | 6/2002 | Fleischmann |
| 2002/0095202 A1 | 7/2002 | Schmidt |
| 2002/0115967 A1 | 8/2002 | Svedman |
| 2002/0127736 A1 | 9/2002 | Chou et al. |
| 2002/0128578 A1 | 9/2002 | Johnston et al. |
| 2002/0150720 A1 | 10/2002 | Howard et al. |
| 2002/0156470 A1 | 10/2002 | Shadduck |
| 2003/0108587 A1 | 6/2003 | Orgill et al. |
| 2003/0225347 A1 | 12/2003 | Argenta et al. |
| 2004/0126413 A1 | 7/2004 | Sigurjonsson et al. |
| 2004/0243073 A1 | 12/2004 | Lockwood et al. |
| 2005/0004534 A1 | 1/2005 | Lockwood et al. |
| 2005/0251083 A1 | 11/2005 | Carr-Brendel et al. |
| 2006/0069340 A1* | 3/2006 | Simon .............................. 604/8 |

FOREIGN PATENT DOCUMENTS

| | | |
|---|---|---|
| WO | WO 02/092783 A2 | 11/2002 |
| WO | WO 2005/046762 A1 | 5/2005 |

OTHER PUBLICATIONS

Kinetic Concepts, Inc., San Antonio, Texas—main page. [online]. Kinetic Concepts, Inc. [Retrieved on Jul. 29, 2004]. Retrieved from the Internet: <URL: http://www.web.archive.org/web/20001202010200/http://kcil.com>. (Web page of Kinetic Concepts, Inc. as archived by archive.org on Dec. 2, 2000.).

New Medicare Code Okays Home Treatment, [online]. Kinetic Concepts, Inc. [Retrieved on Jul. 29, 2004]. Retrieved from the Internet: <URL: http://www.web.archive.org/web/20010124074000/www.kcil.com/vacmedb.html>. (Web page of Kinetic Concepts, Inc. as archived by archive.org on Jan. 24, 2001).

Unger M. A. et al., 2000, "Monolithic Microfabricated Valves and Pumps by Multilayer Soft Lithography," *Science*, 288: 113-116.

VAC Therapy. An Advanced System for Wound Healing [online]. Kinetic Concepts, Inc. [Retrieved on May 14, 2002]. Retrieved from the Internet: <URL: http://www.kcil.com/products/vac/index.asp>.

Whitesides G. M. & Stroock A. D., 2001, "Flexible Methods for Microfluidics," *Physics Today Online*, 1-8.

Wound Care Devices: Vacuum Assisted Closure Therapy: The V.A.C. [online]. Kinetic Concepts, Inc. [Retrieved on Jul. 29, 2004]. Retrieved from the Internet: <URL: http://www.web.archive.org/web/20010302111623/www.kcil.com/the_v.a.c..html>. (Web page of Kinetic Concepts, Inc. as archived by archive.org on Mar. 2, 2001).

Wound Care Devices: Vacuum Assisted Closure Therapy: The mini V.A.C. [online]. Kinetic Concepts, Inc. [Retrieved on Jul. 29, 2004]. Retrieved from the Internet: <URL: http://www.web.archive.org/web/20010112205000/www.kcil.com/mini-v.a.c..html>. (Web page of Kinetic Concepts, Inc. as archived by archive.org on Jan. 12, 2001).

International Search Report from PCT Application No. PCT/US02/18355, dated May 27, 2005 (citing US 5,904,659, 4,817,594, 5,759,570, 4,587,101).

International Search Report from PCT Application No. PCT/US2008/005560, dated Sep. 29, 2008.

* cited by examiner

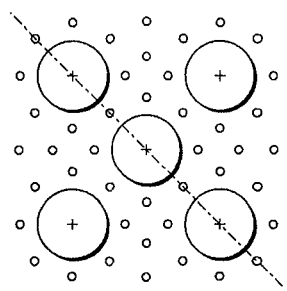
Fig. 2I
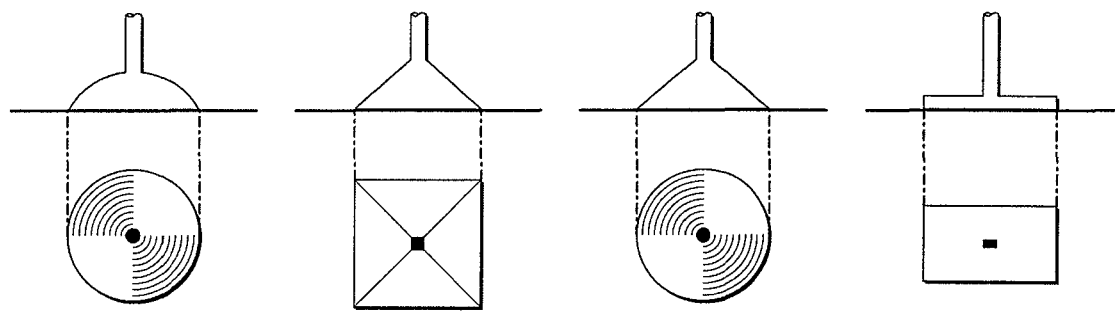
Fig. 2J   Fig. 2K   Fig. 2L   Fig. 2M
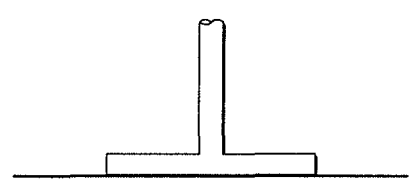 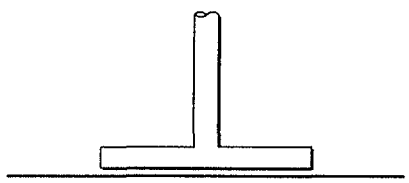
Fig. 2N   Fig. 2O

WOUND HEALING DEVICE

RELATED APPLICATIONS

This application claims priority under 35 U.S.C. §119(e) to U.S. Provisional Application Ser. No. 60/927,069 entitled "Wound Healing Device", filed on May 1, 2007, which is herein incorporated by reference in its entirety.

FIELD OF INVENTION

The invention relates to the promotion of wound healing and tissue growth in general and more specifically to the application of controlled micro-mechanical forces, fluid borne biological mediators and cells via a microfabricated wound therapy apparatus to promote effective tissue growth and/or wound healing in mammals.

DISCUSSION OF RELATED ART

Over one million new chronic wounds develop in the United States each year with estimated treatment costs reaching into the billions of dollars. Wounds can be conceptualized as defects in the protective covering of an individual organ or organ system. Without this physiological barrier, the tissue normally protected by the covering is subject to loss of biologic compartmentalization. When tissue is no longer physiologically compartmentalized it is subject to fluid loss, invasion by microorganisms, electrolyte imbalances, and in some cases metabolic dysfunction. Fluids lost by non-compartmentalized tissue include but are not limited to: blood, plasma, lymph, enteric contents, bile, cerebral spinal fluid, mucus. These fluid losses lead to desiccation of the underlying tissue and enable invasion by microorganisms, leading to potential infection and, in many cases, progressive tissue loss. For example, the inability to heal a chronic skin wound on the lower extremity may lead to amputation of either a portion or all of the effected limb. There are several etiologies for such chronic lower extremity skin wounds, including mechanical trauma, burns, radiation, arterial insufficiency, venous stasis, chronic infection, neuropathy, and systemic diseases such as diabetes. Current methods for improving wound healing emphasize effective drainage, prevention of infection, reduction of inflammation and minimization of tissue and fluid loss.

Most wounds in skin and other organ systems are characterized by a loss of cells and connective tissue matrix from the protective outer layer as well as the underlying layers and tissues. In the case of skin wounds, the epidermis is the outer layer that is lost. The epidermis overlies the dermis as well as deeper structures such as fat, muscle and bone. Closure of large wounds in skin and other organ systems typically requires the production of billions of cells, nutrition through a vascular network and mechanical strength from proteins and glycosaminoglycans present in a nascent extracellular matrix (ECM).

Mechanical forces are well known to have a fundamental role in biologic systems. In development, forces of developing muscles affect bone formation. In addition, the application of mechanical forces has been an important adjunct to surgery. Distraction osteogenesis allows gradual lengthening of bone. Tissue expansion allows gradual lengthening of soft tissues, including nerves and blood vessels. Tension wound-approximation devices close wounds over time. Application of sub-atmospheric pressure to wounds has been shown to increase the vascular supply within the wound and to accelerate healing. Devices and methods for applying micro-mechanical forces to promote wound healing are described in U.S. Published Patent Application No. 2003/0108587.

SUMMARY OF INVENTION

One aspect of this invention relates to devices and methods that permit the controlled application of micro-mechanical forces to a wound surface to promote wound healing and/or tissue growth in mammals. Accelerating wound healing reduces complications including infection, limb loss and pain. Secondary economic gains may result from reduced hospital stays, wound treatments, and medical care for chronically ill patients. The devices and methods disclosed herein also may be used to promote the growth and development of both in vivo and in vitro artificial tissues as well as in vitro tissue explants.

Certain methods of the invention involve a step of protecting the wound site of a subject by covering the wound site with the wound healing apparatus described herein. The method may be carried out by placing the apparatus by itself so as to cover the wound site of the subject, or by placing the apparatus between a medical instrument and the wound site. Medical instruments include for instance catheters, tubes, cannula and plaster.

According to one aspect of the invention, methods and devices are used to locally control mechanical forces applied to tissue on the sub-micron to millimeter scale. Micro-mechanical forces applied to tissues produce localized stress and strain fields in that tissue and stimulate wound healing by promoting cellular proliferation and migration, and stimulating angiogenesis. Devices and methods disclosed herein which apply micro-mechanical forces on a small scale may be used in combination with conventional methods of macroscale force application. These combination devices are capable of concentrating stresses locally to induce precise cellular strains while applying forces over large tissue areas, in some cases to promote wound contraction, and may be adapted to apply forces on a continuous or cyclical basis. Or, in some embodiments, the simultaneous use of a multiplicity of features on the micron to millimeter scale provides a macroscale force application with control on the microscale. This methodology is especially useful for promoting wound healing, however, it also may be useful for stimulating growth or pre-conditioning of tissues in vitro, for example, to increase the wall strength of artificial blood vessels created using tissue engineering approaches.

According to another aspect of the invention, an apparatus for promoting tissue growth includes a biocompatible matrix having a plurality of microstructures, each microstructure being constructed and arranged to apply a mechanical stimulus to a tissue surface. The apparatus is configured such that an application of a first mechanical stimulus by a first microstructure of the plurality of microstructures is separately controllable from an application of a second mechanical stimulus by a second microstructure of the plurality of microstructures.

According to a further aspect of the invention, an apparatus for promoting tissue growth includes a biocompatible matrix having a plurality of microchambers constructed and arranged to face a tissue surface, and each of the plurality of microchambers forms an enclosed perimeter. The apparatus also includes a plurality of channels, with each of the plurality of microchambers being fluidically connected to one or more of the channels. In some embodiments, the channels are microchannels.

According to still another aspect of the invention, a method of applying mechanical stimuli to a target tissue surface to promote tissue growth includes providing a substrate that has a tissue-facing surface which includes a plurality of protruding microstructures. The microstructures have a length to width ratio of less than one hundred to one. The method further includes contacting and maintaining the tissue-facing surface of the substrate against a target tissue surface with a force such that the protruding microstructures deform the tissue surface.

According to another aspect of the invention, microchambers are provided on a wound-facing side of a material matrix. The microchambers are connected to a vacuum source or a pressure source via fluidic microchannels such that each microchamber is able to apply a controlled vacuum or pressure to a small, physically localized area of a wound. The microchambers may be connected to the vacuum source with microchannels controlled by valves such that the forces applied by each microchamber are individually controllable.

According to one aspect of the invention, cell culture chambers are embedded within the material matrix of a wound-healing device. These cell culture chambers produce soluble mediators that are then delivered via microchannels to microchambers or other wound-facing features for application to the wound surface. The soluble mediators may be helpful in promoting wound healing.

According to another aspect of the invention, an apparatus for wound therapy includes a conformable matrix having a plurality of microchambers constructed and arranged to apply physically localized healing stimuli to a wound surface, the application of these stimuli to each of the plurality of microchambers being individually controllable.

According to a further aspect of the invention, an apparatus for wound therapy includes a conformable matrix having a plurality of microchambers constructed and arranged to face a wound surface, with each of the plurality of microchambers forming an enclosed perimeter. Each of the plurality of microchambers is fluidically connected to a microchannel.

According to another aspect of the invention, an apparatus for wound therapy includes a conformable matrix having a multiplicity of chambers and at least two channels fluidically connected to separate chambers or groups of chambers. The apparatus includes valves associated with each channel to individually control the application of one or more of vacuum pressure, positive pressure, wound healing mediators, and cells to each separate chamber or group of chambers.

According to a further aspect of the invention, an apparatus for wound therapy includes a matrix having an open chamber on a face of the matrix, the chamber configured to apply liquid to a wound surface. A cell culture chamber is included within the matrix, with the cell culture chamber being fluidically connected to the open chamber.

According to yet another aspect of the invention, an apparatus for wound therapy includes a conformable matrix having a plurality of chambers constructed and arranged to apply a vacuum pressure to a wound surface. The apparatus also includes a vacuum pressure source. A plurality of channels is included, with each channel being fluidically connected to the vacuum source and connected to at least one of the plurality of chambers. A valve is associated with each channel to control the application of vacuum pressure to the chambers that are fluidically connected to the channel.

According to a further aspect of the invention, a reusable apparatus for wound therapy comprises a silicone rubber matrix having a plurality or microchambers which have a width of 10 microns or less.

In another aspect of the invention, a method for promoting wound healing is provided. The method includes placing a conformable matrix on a wound surface, the matrix having a plurality of microchambers having a width of 10,000 microns or less, and a plurality of microchannels fluidically connected to the microchambers. The method further comprises connecting a vacuum pressure source to the microchannels such that a vacuum pressure is applied to the wound surface.

In another aspect of the invention, an apparatus for wound therapy includes an array of wound healing chambers having a feedback control system employing biosensors to improve or to optimize the wound healing process. The apparatus may include biosensors capable of monitoring a variety of physical and physiological parameters including, but not limited to: pH, dissolved oxygen content, blood hemoglobin concentration, hemoglobin oxygen saturation, bacterial count, toxin concentration, protein concentration and concentrations of metabolic substrates and byproducts. The apparatus includes sensors capable of measuring these physical and physiological parameters via a variety of sensing modalities. The apparatus includes processing circuitry capable of conditioning, transmitting, storing, and mathematically manipulating the measured physical and physiological parameters. The processing circuitry partially comprising the apparatus may include electronic elements, fluidics elements, pneumatic elements, cell-based elements, chemically based elements, optical elements, thermally active elements, or other suitable elements. Other processing function of this circuitry may be conducted by other physical elements of the circuitry not listed herein.

In another aspect of the invention, the an apparatus for wound therapy includes an array of wound healing chambers that are able to apply physically localized mechanical stimuli using various modes of actuation. The modes of mechanical actuation include, but are not limited to those of: ultrasound waves, sound waves, piezoelectric, resistive, thermal expansion and contraction, fluidic, pneumatic, actuation of shape memory alloys and controlled phase transition. Other suitable processing modes of mechanical transduction not listed herein may be used to realize mechanical stimulation of the wound tissue.

According to another aspect of the invention, a method is provided for depositing multiple, physically localized laminates of cells, extracellular matrix, proteins upon the wound bed in order to realize multi-layer, biologically functioning in vivo tissues and materials. This method includes depositing the biological laminates in varying thickness in order to reconstitute the complex barrier function normally provided by the outer surface of an organ or organ system. In the case of a skin wound, this method allows for deposition of a specific combination of cell types in order to recapitulate the structure and function of the dermis. The method allows the deposition of a distinct combination of cell types in order to recapitulate the structure and function of the dermis. The materials deposited using this method may include, but are not limited to: living cells, defunctionalized cells, soluble wound healing mediators, insoluble wound healing mediators, proteins, extracellular matrix proteins, inorganic materials, biodegradable polymers and non-biodegradable polymers. In addition, this method may include the capacity to deposit parenchyma cells in order to reconstitute organ function.

In another aspect of the invention, an apparatus for wound therapy includes a surface in contact with the wound bed, and the surface may demonstrate variety of surface textures ranging from sub-micron feature sizes to surface structures on the micron to millimeter scale. For the purposes of describing this aspect, feature size refers to the spatial period and spatial amplitude of surface variations that make up the surface texture. Within this apparatus, these textures may exist with a variety of periodic shapes including, but not limited to: sine wave, saw tooth wave, square wave, random amplitude, triangle wave, or other suitable shape. The surface texture of the apparatus may include multiple surface textures superimposed upon each other either with a distinct or a similar spatial period and or spatial amplitude. The texture of the surface may be realized via a variety of fabrication methods including, but not limited to: microlithography, soft lithography, peening, deposition of particulates, deposition of thin films, deposition of proteins, plasma etching, and deposition of nanofabricated materials including nanoparticles and/or nanotubes.

Other embodiments of the invention are described below or are captured by the claims recited below.

BRIEF DESCRIPTION OF THE DRAWINGS

The accompanying drawings are not intended to be drawn to scale. For purposes of clarity, not every component may be labeled in every drawing. In the drawings:

FIG. 2i shows a plan view of an alternative embodiment of microchambers constructed and arranged to apply localized micromechanical stimuli to a wound surface;

FIG. 2j shows a cross-sectional side view and a bottom view of one embodiment of an individual microchamber constructed to apply micromechanical stimuli to a wound surface;

FIG. 2k shows a cross-sectional side view and a bottom view of an alternative embodiment of an individual microchamber constructed to apply micromechanical stimuli to a wound surface;

FIG. 2l shows a cross-sectional side view and a bottom view of an alternative embodiment of an individual microchamber constructed to apply micromechanical stimuli to a wound surface;

FIG. 2m shows a cross-sectional side view and a bottom view of an alternative embodiment of an individual microchamber constructed to apply micromechanical stimuli to a wound surface;

FIG. 2n shows a cross-sectional side view of an alternative embodiment of an individual microchamber constructed to apply micromechanical stimuli to a wound surface;

FIG. 2o shows a cross-sectional side view of an alternative embodiment of an individual microchamber constructed to apply micromechanical stimuli to a wound surface;

DETAILED DESCRIPTION OF PREFERRED EMBODIMENTS

Figure 1A:
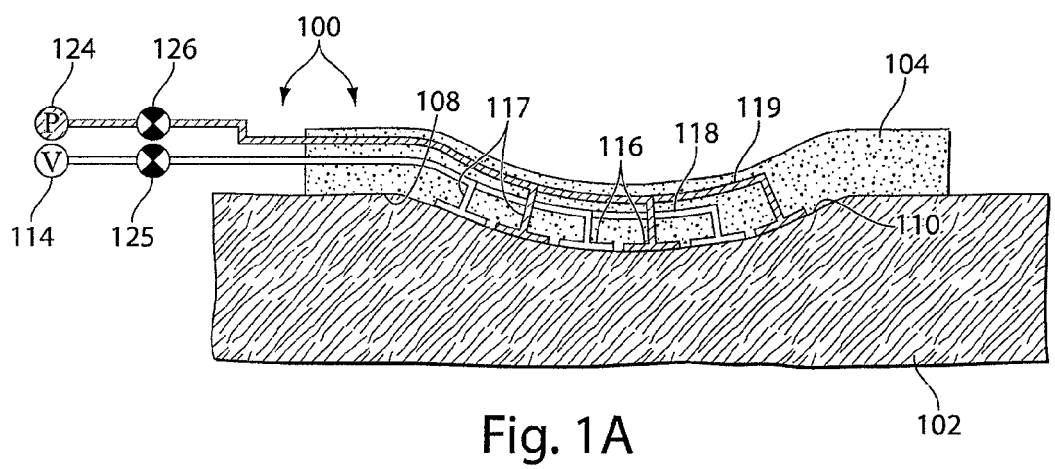
FIG. 1a shows a cross-sectional side view of one embodiment of a wound therapy device including microchannels fluidically connected to microchambers.
Figure 1B:
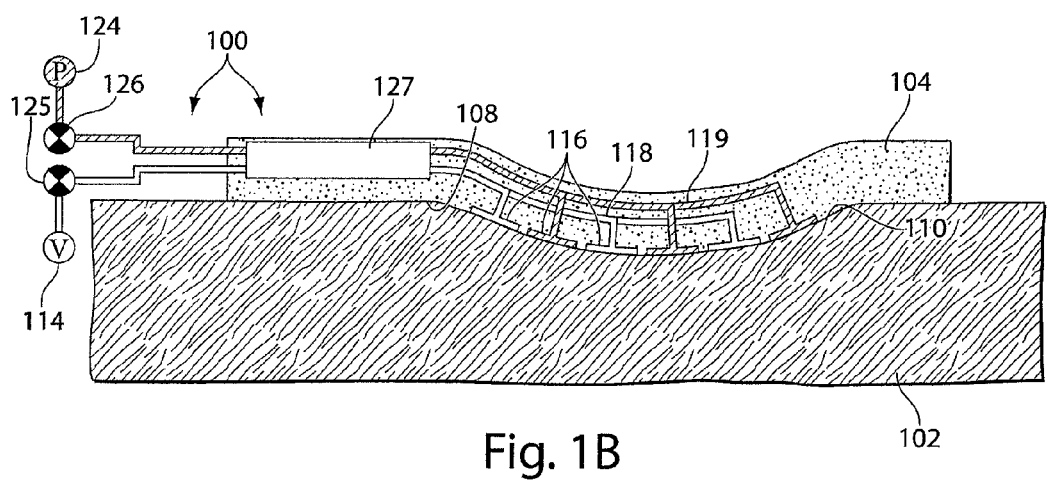
FIG. 1b shows a cross-sectional side view of one embodiment of a wound therapy device including microchannels fluidically connected to microchambers and a network of control circuitry.
Figure 1C:
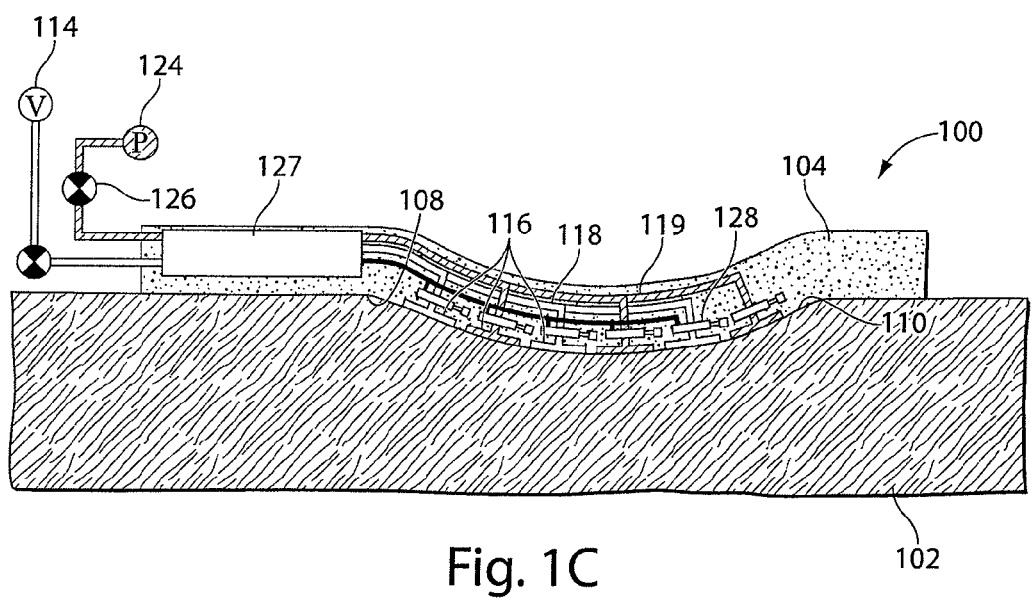
FIG. 1c shows a cross-sectional side view of one embodiment of a wound therapy device including microchannels fluidically connected to microchambers, a network of control circuitry and a series of inlet flow control lines.

Physical forces that are applied to tissues at the macroscopic scale are redistributed to the microscale to affect individual cellular form and function. However, when these forces are applied homogeneously over large areas, the level of strain or deformation experienced by individual cells can be quite small, thus limiting the cellular response. In addition, global force applications typically result in a wide variety of stresses within a wound. Devices are currently available that assist in wound healing by applying mechanical forces on the macroscale (evenly over areas greater than 1 cm$^2$) including: tension wound closure devices; vacuum assisted closure devices; and devices applied in distraction osteogenesis. According to one aspect of the invention, locally concentrated forces are applied within multiple smaller regions (in some embodiments less than 1 mm$^2$, and in some embodiments less than 100 microns$^2$), so as to amplify and in some cases optimize the forces that are experienced by individual cells. One advantage of certain embodiments of this method of micromechanical force application is the ability to induce cell stretch without increasing the size of the wound, thus reducing the likelihood of wound dehiscence. One manner of applying localized forces is to separately control the application of vacuum pressure and/or positive pressures to separate chambers that act on the wound surface.

Cells within the wound can be subjected to a controlled strain using devices that mechanically induce tension or compression in a steady or time-dependent manner as necessary. These devices also may be fabricated to enable local delivery of soluble and insoluble mediators as well as pharmacologically active agents.

To apply controlled, localized forces to a wound surface, according to some embodiments of the invention, a number of microchannels are fluidically connected to microstructures, such as microchambers for example, within a matrix that can be positioned on a wound surface. Vacuum pressure (or positive pressure) applied to each microchamber is controlled via the microchannels. The term "vacuum pressure," for purposes herein, refers to a pressure in a chamber or material of interest that is lower in magnitude than of a reference chamber, material, tissue, or atmosphere. The term "positive pressure", for purposes herein, refers to a pressure in a chamber or material of interest that is higher in magnitude than that of a reference chamber, material, tissue, or atmosphere. The term "pressure", for purposes herein, is intended to encompass both vacuum pressure and positive pressure.

The term "wound," for purposes herein, refers broadly to an injury to an organ or organ system. In the case of the skin, the injury may be to the epidermis, the dermis and/or the subcutaneous tissue. Skin wounds may be classified into one of four grades depending on the depth of the wound: i) Grade I: wounds limited to the epithelium; ii) Grade II: wounds extending into the dermis; iii) Grade III: wounds extending into the subcutaneous tissue; and iv) Grade IV (or full-thickness wounds): wounds wherein bones are exposed (e.g., a bony pressure point such as the greater trochanter or the sacrum). The term "partial thickness wound" refers to wounds that encompass Grades I-III; examples of partial thickness wounds include burn wounds, pressure sores, venous stasis ulcers, and diabetic ulcers. The term "deep wound" includes both Grade III and Grade IV wounds. The methods of the invention are useful for treating all grades of wounds, including chronic and acute wounds. The term "chronic wound" refers to a wound that has not healed within 30 days.

The term "promoting wound healing," for purposes herein, refers to enabling reconstitution of the normal physiologic barrier of an organ or organ system. In the case of skin wounds, promoting would healing may include the induction of the formation of granulation tissue, and/or the induction of wound contraction, and/or the induction of revascularization, and/or the induction of epithelialization (i.e., the generation of new cells in the epithelium).

The types of wounds to be treated by the methods of the invention include various kinds of wounds including, but are not limited to: surgical wounds; traumatic wounds; radiation injury wounds; toxic epidermal necrolysis wounds; infectious wounds; neoplastic wounds; full-thickness wounds; partial-thickness wounds; and burn wounds, as well as wounds arising from various types of ulcers, such as skin ulcers, corneal ulcers, arterial obstructive ulcers, continuous pressure-induced decubital and diabetic ulcers, burn ulcers, injury ulcers, radiation ulcers, drug-induced ulcers, post-operative ulcers, inflammatory ulcers, ulcers of the gastrointestinal tract, simple ulcers and other types of angiopathic ulcers, and chronic (intractable) ulcers.

The methods of various embodiments of the invention may be particularly useful in treating complex wounds or difficult-to-heal wounds. Many factors can adversely affect the wound healing process, including infection, radiated tissue, systemic illness, medications, patient age, patient health, and the nutritional status of the subject. In addition, any process that impedes peripheral blood circulation, such as arteriosclerosis, prolonged pressure, varicose vein disease, and venous stasis, can adversely affect the delivery of oxygen, nutrients, chemical signals, and appropriate cell types to mediate healing in an injured subject, will impair wound healing. Factors which inhibit wound healing include wound desiccation, medication, such as chemotherapy or steroids, and poor patient health and/or nutrition. Certain partial and full thickness injuries, such as burns, skin grafts, and various types of ulcers, resist repair and produce significant pain and discomfort for the subject.

The general physical condition of the patient is also important in wound healing. As age increases, the ability to repair injured tissue decreases as the skin becomes thinner and the number of fibroblasts and amount of total skin collagen decrease. Disease states such as alcoholism, anemia, diabetes, malnutrition, shock, and uremia lead to impaired oxygen and nutrient delivery to the wound site, thereby inhibiting the healing process. Also, diseases leading to monocytopenia can significantly impair wound healing.

Medications used to treat disorders can produce impaired wound healing. Chemotherapy, used to eliminate dividing cells in cancer patients, also suppresses the ability of such a patient to heal wounds, which is also dependent upon new cell growth. Steroids negatively impact all three phases of wound repair, inhibiting the initial inflammatory response, slowing the production of new epithelium and vascular tissue, and weakening the collagen matrix in the scar tissue.

Bacterial wound infection is a common local cause for prolonged wound healing. Human skin is typically colonized by a number of microorganisms, including *Candida albicans, Staphylococcus epidermidis, Staphylococcus aureus*, and some *Streptococcus* strains. Thus, any wound which exposes underlying tissues to the environment becomes infected with at least resident microbial flora. Wounds which are well tended and in highly vascularized tissue resist infection, while those in ischemic tissue are much more susceptible to infection.

Wound healing involves fibrin clot formation, recruitment of inflammatory cells, re-epithelialization, and matrix formation and remodeling. Immediately after tissue injury, blood vessel disruption leads to the extravasation of blood and concomitant platelet aggregation and blood coagulation resulting in fibrin clot formation. Activated platelets trapped within the fibrin clot degranulate and release a variety of cytokines and growth hormones. These cytokines and growth hormones help to recruit inflammatory cells to the site of injury, to stimulate angiogenesis, and to initiate the tissue movements associated with re-epithelialization and connective tissue contraction.

Neutrophils and monocytes are recruited to the site of injury by a number of chemotactic signals including the growth factors and cytokines released by the degranulating platelets, formyl methionyl peptides cleaved from bacterial proteins, and the by-products of proteolysis of fibrin and other matrix proteins. Neutrophil infiltration ceases after a few days, but macrophages continue to accumulate by continued recruitment of monocytes to the wound site. Activated macrophages release growth factors and cytokines thereby amplifying the earlier signals from the degranulating platelets. Exogenous factors can be applied to the wound to aid in these processes.

Thus, embodiments of the invention also include methods which involve the inclusion of soluble factors and/or cells which produce soluble factors, naturally or which are produced using recombinant techniques, in the apparatuses described herein. Following placement of the apparatus on the wound, the soluble factors added to the apparatus or produced by the cells (e.g., growth factors like epidermal growth factor, cytokines, PGDF, insulin like growth factor, TGF-beta, keratinocyte growth factor cytokine, TNF, chemokines, chemotactic peptides, tissue inhibitors of metalloproteinases, etc.) pass into the liquid in the microchannels and can be delivered to the wound in a controlled manner.

The soluble factors may be applied to the wound surface through microchannels that lead to the microchambers. For example, PDGF, EGF, GM-CSF, FGF and other suitable mediators may be carried to the microchambers by the microchannels.

In addition to the desirable wound therapy effects described above, control of the individual microchambers may permit the performance of multivariable studies on a single wound surface to investigate the effects of varying wound healing parameters such as vacuum pressures applied and soluble mediators used.

Soft lithography may be used to manufacture the matrix according to one aspect of the invention. The microchambers and associated microchannels may be formed during the stacking and bonding of layers of material such as silicone rubber and/or polydimethyliloxane (PDMS). Other materials that may be used in various embodiments disclosed herein include: elastomeric polymers, biodegradable polymers, poly-lactic-co-glycolic acid (PLGA), plastics, metals, and gels.

In an alternative embodiment, each microchannel may be fluidically connected to a group of microchambers for applying vacuum pressure. The soluble mediators may be added to the microchambers through the same microchannels (i.e., the vacuum pressure channels) by alternating the application of a vacuum pressure and the introduction of the mediators to the microchambers. In some embodiments, soluble mediators may be introduced into the microchambers through a first microchannel, and a second microchannel may be connected to a vacuum source. In such embodiments, the application of a vacuum pressure to the second microchannel may pull or help pull mediators into the microchambers from the first microchannel.

Individualized control of the pressures and/or mediators that are applied to each microchamber may be achieved by arranging valves to control fluid flow through the microchannels. In some embodiments, the valves may be embedded within the structure that is placed over the wound surface. For example, pneumatically-controlled microfluidic valves may be formed during manufacture of the matrix, and these valves may be used to selectively turn on or turn off vacuum pressure to a particular microchamber, or change the level of vacuum pressure in the microchamber. In this manner, a single vacuum source providing a constant vacuum pressure may be used, yet the vacuum pressure applied to different areas of the wound surface via the various microchambers is adjustable, or even non-existent in some microchambers.

Valves used in the wound therapy device may be manually actuated or may be responsive to a controller. In some embodiments, feedback from sensors which trace the state of the wound maybe used as input data for the controller.

In some embodiments, check valves, switch valves, microfluidic pumps, microfluidic compressors, microfluidic regulators, and/or other microfluidic components may be used as part of the control of fluid flow to and/or from each microchamber. For example, in some embodiments, microchannels which deliver mediators to a microchamber may include a check valve to prevent backflow or clogging of the microchannel when a positive pressure is applied to the microchamber by another microchannel. Various types of microfluidic valves and pump and methods of fabrication thereof can be found in U.S. Patent Application Publication No. 2002/0127736, which is hereby incorporated by reference.

Various soluble mediators that may be used to promote wound healing typically are produced by living cells. A continuous source of soluble mediators for application to the wound surface may be achieved by embedding cell culture chambers within the matrix. Similar to the embedding of microfluidic valves, cell culture chambers may be formed during the manufacture of the matrix. The cell culture chambers may be constructed and arranged to support fibroblasts, endothelial cells, eosinophils, megakaryocytes, stem cells, or other suitable cells. Valves, pumps, or other microfluidic components may be used to control the release of the mediators produced by these cells.

Embodiments of the invention may comprise coating wound-facing portions of a wound healing device with extra cellular matrix (ECM) factors to stimulate cell growth. In some embodiments, ECM factors may be used within a chamber to promote adhesion of cells to a chamber wall. Portions of the device may be coated with peptide fragments, synthetic molecules and/or growth factors to enhance cell proliferation and wound healing.

As described in more detail below, micro-mechanical force application may be combined with exogenous growth factors and cytokines. In some embodiments micro-mechanical force application is controllable along with soluble mediator delivery, and feedback may be used to adjust operation parameters. In some embodiments, acts of controlling delivery of drugs, proteins, and other factors may be employed to control edema, minimize infection and inflammation, and facilitate wound healing. According to some embodiments of the invention, materials may be fabricated with sub-micron to millimeter sized features, such as microchambers, which locally direct vacuum pressure or positive pressure on cells.

One embodiment of a wound therapy device 100 is shown positioned on a subject's wound 102 in FIG. 1a. A conformable matrix 104 includes a wound-facing surface 108 which is placed in contact with a wound surface 110. The term "subject" refers to both humans and non-human animals. Subjects may include any human or non-human animal in which promoting tissue growth is desirable. Wound-facing surface 108 includes an array of microchambers 116 which are fluidically connected to a vacuum source 114 through a network of microchannels 117. Six microchannels are illustrated in FIG. 1a as being fluidically connected to microchambers, but greater (or lesser) numbers of microchannels may be used, for example, 100 microchannels, 1000 microchannels, 10,000 microchannels, or 100,000 microchannels or more. Microchannels 117 may be connected to vacuum source 114 via manifolds 118, 119, and numerous manifolds may be used. In some embodiments, groups of microchannels may be connected to a single microchannel with a manifold, and the single microchannel in turn may be connected to another manifold. In this manner, microchannels 117 may branch in steps from a channel 120 connected to vacuum source 114 such that thousands of microchannels are present in the vicinity of the microchambers at wound-facing surface 108. In some embodiments, an embedded control interface 127 determines which manifolds are activated and/or connected to the vacuum pressure source 114 or the positive pressure source 124. In some embodiments, this control interface is involved with the generation and regulation of vacuum pressure and positive pressure. In some embodiments, microvalves 128 which are co-located with the microchambers determine flow of fluid in and out of the microchamber as well as which microchambers are connected to the vacuum pressure source 114 and/or positive pressure source 124.

The terms "channel" and "microchannel", as used herein, refer to defined pathways through which a fluid may travel. A microchannel generally has at least one dimension that is less than 1000 microns. For example, a microchannel may have a width of 1000 microns, 100 microns, 10 microns, 1 micron or less, or any suitable width less than 1000 microns. The definition of channel encompasses microchannels. Channels and microchannels do not require a specific structure, but the terms are not meant to encompass pathways which are formed only when a flow of fluid develops. For example, the relatively random flow of gas or liquid through the interspersed voids of a foam pad is not considered to be flow through a channel or microchannel for purposes herein.

The terms "chamber" and "microchamber", as used herein, refer to volumes defined by walls which are sufficient to create a substantially closed volume when the chamber or microchamber is placed against a wound surface or other tissue surface (whether in vivo or in vitro). A microchamber, which is included within the definition of chamber, generally has at least one dimension that is less than or equal to 10,000 microns. For example, a circular microchamber may have a diameter of 10,000, less than 1000 microns, less than 100 microns, less than 10 microns, less than 1 micron or less, or any suitable width less than 10,000 microns.

The term "microstructure", as used herein, refers to a structure that has at least one dimension that is less than or equal to 10,000 microns. The term microstructure encompasses defined volumes, such as, for example, microchambers. In some embodiments, a microstructure may have at least one dimension that is less than 10,000 microns, less than 1000 microns, less than 100 microns, less than 10 microns, or 1 micron or less.

The term "protruding microstructure", as used herein, refers to a structure that has at least one dimension that is less than or equal to 10,000 microns and protrudes from a base surface. In some embodiments, a protruding microstructure may have at least one dimension that is less than 10,000 microns, less than 1000 microns, less than 100 microns, less than 10 microns, or 1 micron or less. A microchamber and the walls of a microchamber are not encompasses by the definition of a protruding microstructure.

Matrix 104 may be manufactured using a variety of manufacturing methods, including soft lithography, bulk machining, and surface micromachining. It is to be understood that the present invention is not necessarily limited to fabrication by one or more of the methods described herein as other suitable fabrication methods may be employed.

Soft lithography may include stacking and bonding layers of PDMS and/or silicone rubber. The flexible qualities of these materials permit matrix 104 to be conformable in some embodiments so that matrix 104 may contact all or substantially all of the portion of wound surface 110 that it overlays. The matrix also may be manufactured to be transparent so that direct visual inspection of the wound is possible. In some embodiments, a portion of matrix 104 is transparent while other portions are opaque. In some embodiments, all of matrix 104 is opaque. In many embodiments, matrix 104 directly contacts wound surface 110 with wound-facing surface 108. In some embodiments, the wound-facing surface of matrix 104 does not directly contact wound surface 110 in that a thin membrane or material layer may be disposed between matrix 104 and the wound surface.

In some embodiments, matrix 104 or portions of matrix 104 may be formed with various materials such as thermoplastic materials and/or thermoset materials. Examples of thermoplastic materials include: polyolefins; polyesters; polyamides; polyvinylchloride; polyether esters; polyimides; polyesteramide; polyacrylates; polyvinylacetate; and hydrolyzed derivatives of polyvinylacetate. Examples of thermoset materials include: polyurethanes; acrylates; epoxies; and silicones. In some embodiments, matrix 104 or portions of matrix 104 may be formed with biodegradable polymer materials. Examples of biodegradable polymer materials include, but are not limited to: poly-lactic-co-glycolic acid (PLGA), poly(dioxanone), poly(trimethylene carbonate) copolymers, and poly (ε-caprolactone) homopolymers and copolymers. In some embodiments, matrix 104 may be formed using inorganic materials such as glass, ceramics, or metals.

In some embodiments comprising fabrication using soft lithography, pre-cured elastomer layers are assembled and bonded together chemically. In some embodiments of bonding, the elastomeric layers are composed of the same elastomeric material, with the same chemical entity in one layer reacting with the same chemical entity in the other layer to bond the layers together. In some embodiments, bonding between polymer chains of similar elastomer layers may result from activation of a crosslinking agent due to light, heat, or chemical reaction with a separate chemical species.

Elastomeric layers may be cast on a micro-machined mold. The micro-machined mold may be constructed by any suitable method, for example, photolithography, ion-milling, or electron beam lithography.

A pressure source 124 may be connected to channel 120 to apply pressure to various microchambers. In some embodiments, separate microchannels may lead from pressure source 124 to various microchambers or other components so that mediators, drugs or other factors may be added to a microchamber while the chamber is experiencing a vacuum pressure.

Various of the channels and/or microchannels may include valves that are external to matrix 104 (such as valves 125, 126), or embedded within matrix 104 (see description of FIG. 3a further below). The valves permit selective application of pressures (including vacuum pressure) to the microchambers. Valves associated with the wound therapy device may be manually operable or automated. In the case of automated valves, the valves may be actuated by a controller in response to sensor readings taken from within the wound bed.

Figure 2A:
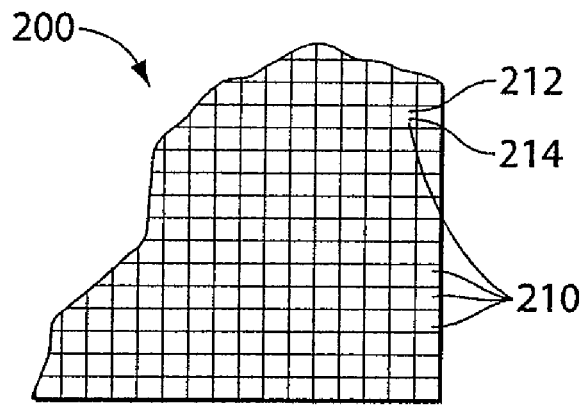
FIG. 2a shows a plan view of one embodiment of microchambers constructed and arranged to apply localized micromechanical stimuli to a wound surface.
Figure 2B:
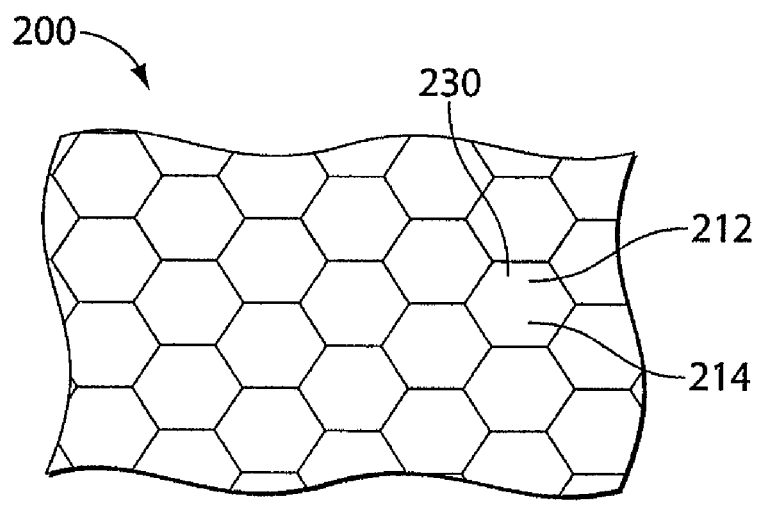
FIG. 2b shows a plan view of an alternative embodiment of microchambers constructed and arranged to apply localized micromechanical stimuli to a wound surface.
Figure 2C:
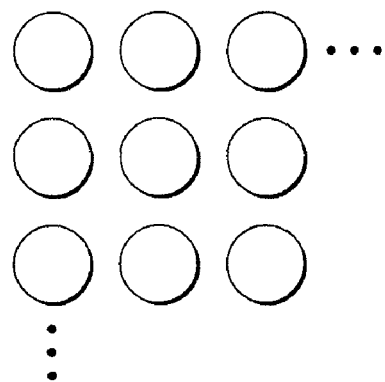
FIG. 2c shows a plan view of an alternative embodiment of microchambers constructed and arranged to apply localized micromechanical stimuli to a wound surface.
Figure 2D:
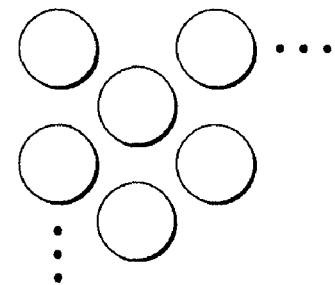
FIG. 2d shows a plan view of an alternative embodiment of microchambers constructed and arranged to apply localized micromechanical stimuli to a wound surface.
Figure 2E:
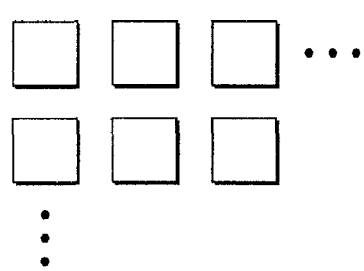
FIG. 2e shows a plan view of an alternative embodiment of microchambers constructed and arranged to apply localized micromechanical stimuli to a wound surface.
Figure 2F:
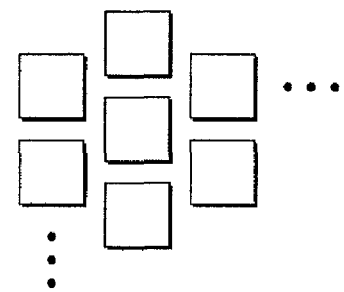
FIG. 2f shows a plan view of an alternative embodiment of microchambers constructed and arranged to apply localized micromechanical stimuli to a wound surface.
Figure 2G:
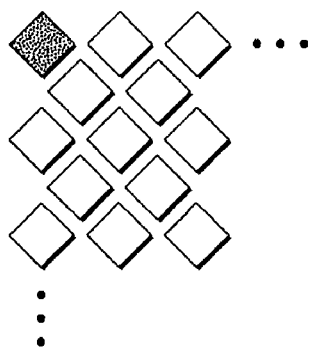
FIG. 2g shows a plan view of an alternative embodiment of microchambers constructed and arranged to apply localized micromechanical stimuli to a wound surface.
Figure 2H:
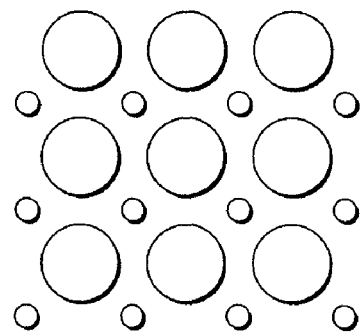
FIG. 2h shows a plan view of an alternative embodiment of microchambers constructed and arranged to apply a localized micromechanical stimuli to a wound surface.

A section of a one embodiment of an array of microchambers 210 positioned on a wound-facing side 200 of matrix 104 is illustrated in FIG. 2a. In this embodiment, the microchambers are square or substantially square, but in other embodiments, any suitable and physically realizable three dimensional geometry may be used. For example, as shown in FIG. 2b, hexagonal or substantially hexagonal microchambers 230 may be arranged such that a wound treatment area of wound therapy device 100 is substantially entirely covered with microchambers. Microchambers of different shapes may be used on the same wound healing device. Included in some embodiments are microchambers with three dimensional geometries that may be dynamically changed, either in a predetermined manner or in response to the conditions of the wound or other variable parameters. In some embodiments, microchambers may not cover the entire wound treatment area. For example, circular or substantially circular microchambers may be used in some embodiments, thereby leaving areas between the microchambers which do not form vacuum-capable chambers. In some embodiments, microchambers of different shapes may be used to cover all or substantially all of the wound treatment area of the wound treatment device.

All of the microchambers of a wound healing device may be the same size, or, in some embodiments, varying sizes may be used in certain areas or throughout the wound treatment area. In some embodiments, each side of microchamber 210 is approximately 10 microns or smaller. In some embodiments, each side of microchamber 210 is 100 microns. For hexagonal microchambers 230, the distance from one corner to the opposite corner is approximately 10 microns in some embodiments, and approximately 100 microns in some embodiments. Other suitable sizes for microchambers 230 may be used. For purposes herein, the "width" of a microchamber refers to a maximum lateral dimension of the microchamber.

The shape and size of the microchambers may be designed using computer design and analysis, for example, finite element analysis, to provide estimates of levels of local stresses and/or mediator delivery.

FIGS. 2c-2o show various embodiments of shapes and arrangement of microchambers.

Each of the microchambers may be fluidically connected to one or more microchannels which enter the microchamber via ports. In the illustrated embodiment, a first port 212 fluidically connects microchamber 210 to a microchannel (not shown) which leads to a vacuum source. Various valves, manifolds, or additional microchannels or channels may be interposed between microchamber 210 and the vacuum source. A second port 214 fluidically connects microchamber 210 to a source of soluble mediators, such that mediators can be controllably introduced into microchamber 210. Microchamber 210 may include further ports or microfluidic interconnections.

To effect individual control of the application of pressure to the microchambers, each microchannel may have an associated valve. For purpose herein, the phrase "individually controllable", as referring to the application of vacuum pressure, positive pressure, or other delivery of force or signals to a microchamber, or media delivery within a microchamber, means the ability to control one or more of these factors in a microchamber (or a group of microchambers) without substantially changing the same factor(s) in another microchamber of the wound therapy device. The term "controlling", as referring to controlling a factor such as, for example, the vacuum pressure (or positive pressure or media delivery) in a microchamber is intended to encompass switching the factor (such as a vacuum pressure or a positive pressure or media delivery) on or off, and also is intended to encompass changing the magnitude of the factor. Also for purposes herein, the terms "variable vacuum pressure" and "variable positive pressure" mean a pressure having a magnitude which can be changed with or without entirely eliminating the pressure. The term, "pressure", as used herein, encompasses both vacuum pressure and positive pressure.

In some embodiments, channels or microchannels may be fluidically connected to chambers or microchambers to remove liquid from the wound surface. In some embodiments, microchannels or other elements may be configured to remove colloids, solids, vapors and/or gases from tissue.

Figure 3A:
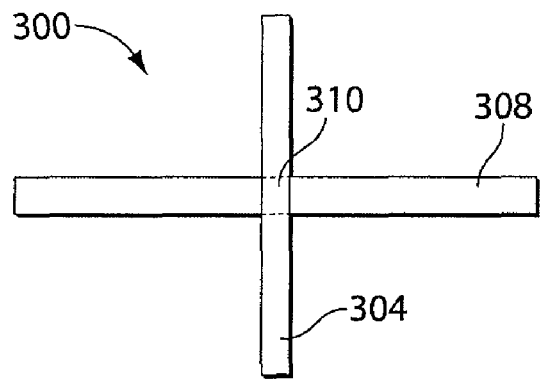
FIG. 3a is a top view of one embodiment of a microfluidic valve.
Figure 3B:
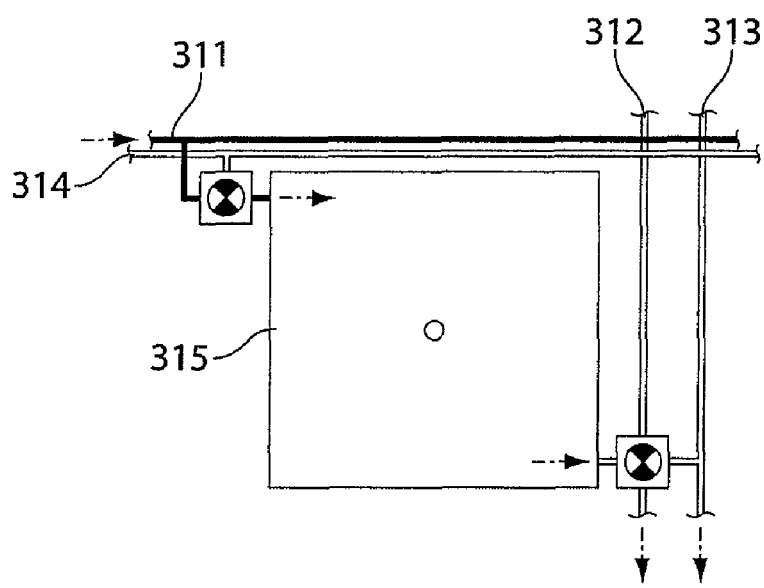
FIG. 3b is a schematic top view of one embodiment of the valve configuration that enables independent addressability of individual microchambers within the network of microchambers.

FIG. 3a shows one embodiment of an on/off microfluidic valve 300 that may be embedded on the matrix of the wound healing device. Valve 300 has a crossed-channel structure which includes a 30-micron wide control line 304 positioned on top of a 50-micron wide flow line 308. A thin membrane 310 of PDMS (or other suitable material), e.g., approximately 30 microns thick, is present between control line 304 and flow line 308. When pressure is applied to top control line 304, for example by pressurizing control line 304 with air, membrane 310 is pushed downward to restrict or close flow line 308. Control line 304 may be pneumatically activated, and numerous valves may be densely packed on the matrix. Independent control of flow in and out of each microchamber may be realized via embedded microvalves such as is illustrated in FIG. 3b whereby an open connection between an inflow line 314 and a microchamber 315 is realized via a horizontal or row selection line 311. In a similar manner, open connection between an outflow line 313 and the microchamber 315 may be realized via a vertical or column selection line 313.

The shapes and/or sizes of the control line and the flow line may be different than those of the illustrated embodiment, and are not intended to be limiting. Microfluidic pumps may be created by positioning several control lines adjacent to one another on the flow line. In some embodiments of the invention, soluble mediators or drugs may be delivered to a microchamber using such a microfluidic pump, or other suitable microfluidic pump. By progressively actuating the control lines, fluid may be pumped along the flow line. Combinations of valves may be used to form switches, and in some embodiments, valves may be configured to permit reverse flow in various microchannels. Reverse flow may allow flushing, cleaning or unclogging of microchannels.

In some embodiments, microfluidic compressors, regulators, vacuum pumps and/or other microfluidic components may be embedded within an apparatus such that attachment to external sources of pressure is not needed. In some embodiments, various of the microfluidic components may be controlled and/or actuated with electrical power, and in some cases, the apparatus may be powered by battery power and portable.

Figure 4:
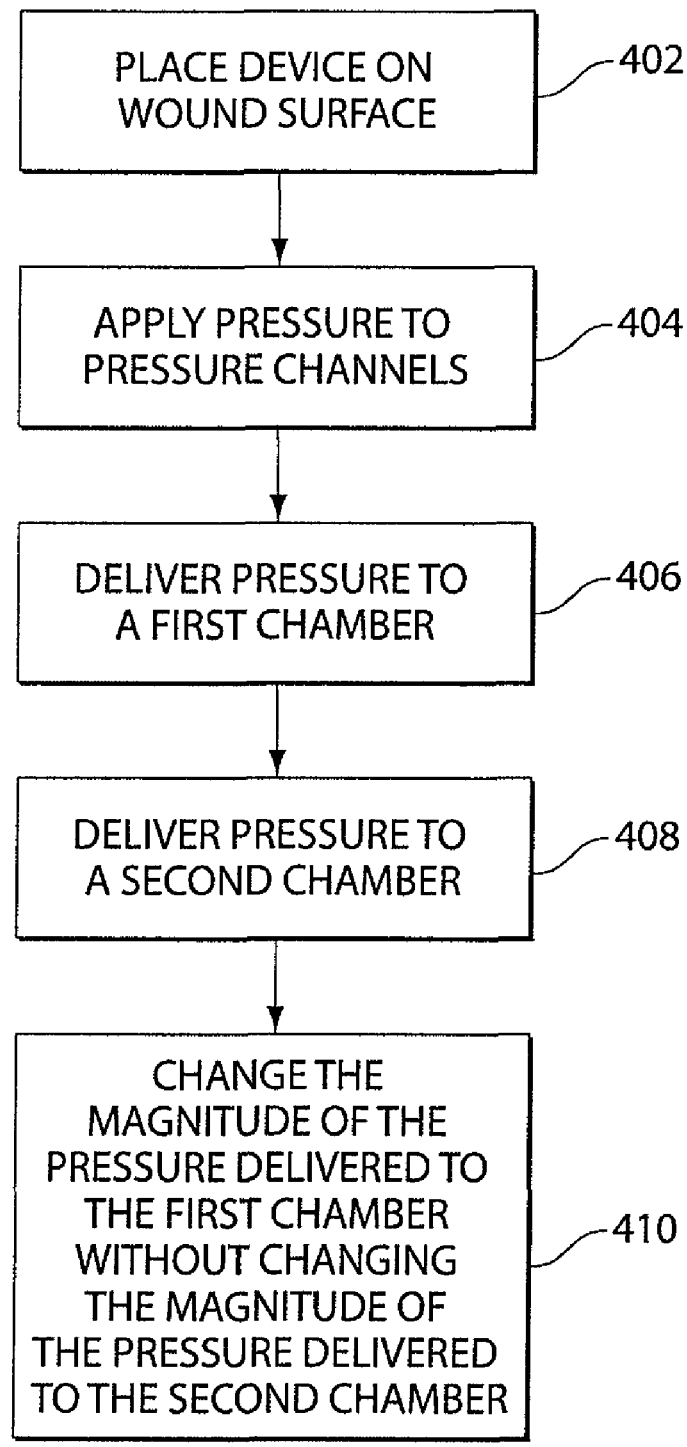
FIG. 4 is a flow chart illustrating one embodiment of a method of using a wound therapy device.

A method 400 of using a wound therapy device is shown by way of a flowchart in FIG. 4. In an act 402, the device is placed on a wound surface such that pressure chambers (e.g., microchambers) face the wound surface. The device need not entirely cover the wound, and/or it may extend beyond the perimeter of the wound. Pressure is applied to the pressure channels of the device in an act 404. A vacuum pressure may be applied by connecting a vacuum pump or other vacuum source to the device such that the vacuum source may be fluidically connected to a network of channels which fluidically connect to the pressure chambers. In some embodiments, a positive pressure source is also connected to the device, and may be fluidically connected to a separate network of channels which fluidically connect to the chambers.

In an act 406, pressure is delivered to a first pressure chamber at a first magnitude. In an act 408, pressure is delivered to a second pressure chamber at a second magnitude. The second magnitude may be the same or different as the first magnitude. Without changing pressure in the second pressure chamber (i.e., the second magnitude), the magnitude of the pressure delivered to the first chamber (i.e., the first magnitude) is changed in an act 410. In this manner, the magnitudes of the pressures delivered to the two chambers are individually controllable. As described herein, the pressure magnitudes may be controlled with valves, including microfluidic valves. In some embodiments, hundreds, thousands, or millions of pressure chambers may be present on the device, and a single valve may be associated with a small or large number of pressure chambers. As described herein, a single microfluidic valve or microchamber may be associated with a small or large number of microfluidic valves and or microfluidic channels.

Figure 5A:
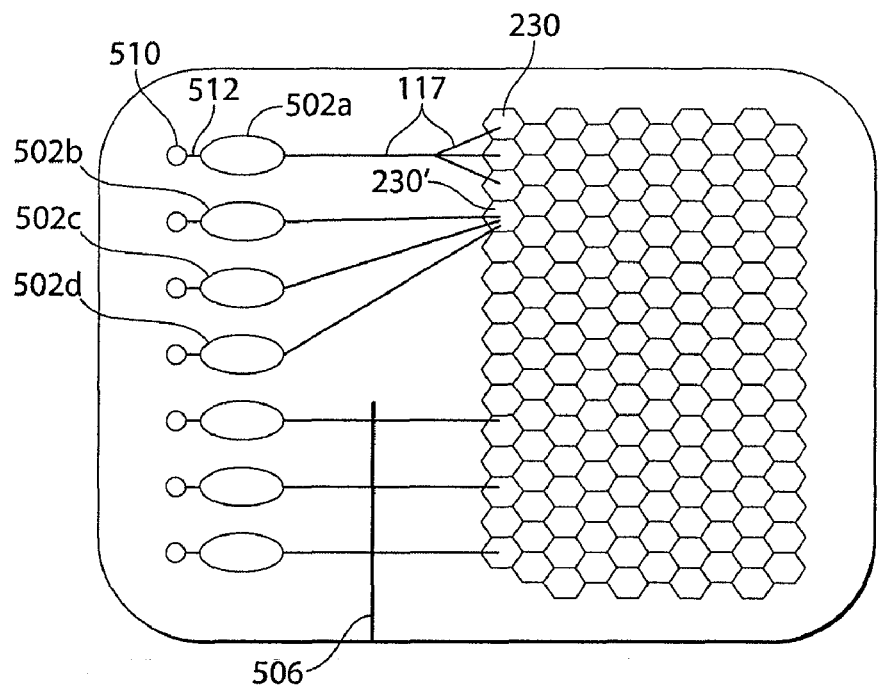
FIG. 5a is a top view of one embodiment of a wound therapy device including embedded cell culture chambers.

To locally produce soluble mediators, the matrix of the wound healing device may include cell culture chambers formed within the matrix itself. As shown in FIG. 5a, a cell culture chamber 502a is fluidically connected to several microchambers 230 via microchannels 117. Cell culture chamber may include cells such as fibroblasts, endothelial cells, eosinophils, megakaryocytes, stem cells, or other suitable cells, to produce soluble mediators. As the mediators are produced, they may be delivered to microchambers 230 to aid in wound treatment. Delivery of mediators may occur continuously, on a regular periodic basis, or in response to specific instructions from a controller. Vacuum pressure from microchambers 230 may draw the soluble mediators from cell culture chamber 502a to microchambers 230, or, in some embodiments, pressure may be supplied to cell culture chamber 502 to push the soluble mediators to microchambers 230. The various features illustrated in FIG. 5a are not intended to be drawn to scale.

A substratum of extracellular matrix may be coated onto the microchannel surface before application of cells, particularly if the cells are adherent or anchorage-dependent cells. Generally anchorage-dependent cells requires attachment to a surface and spreading out in order to grow. The term "extracellular matrix" refers broadly to material for supporting cell growth, including, but not limited to, material that is distributed throughout the body of multicellular organisms such as glycoproteins, proteoglycans and complex carbohydrates. Although the invention is not limited by the nature of the extracellular matrix, the available extracellular matrices include Matrigel, Growth Factor Reduced Matrigel, fibrillar collagen, laminin, fibronectin and collagen type IV.

It has been noted that a number of recombinant growth factors may accelerate the wound healing process, in both acute and chronic wounds, in animal models. These recombinant derived factors include Platelet-Derived Growth Factor (PDGF), Fibroblast Growth Factor (FGF), Epidermal Growth Factor (EGF), and Transforming Growth Factors $\alpha$ and $\beta$ (TGF-$\alpha$ and TGF-$\beta$). Additionally, other recombinant growth factors, including insulin, Insulin-like Growth Factors I and II (IGF-I and IGF-II, respectively), Interferons (IFNs), Interleukins (ILs), KGF (Keratinocyte Growth Factor), Macrophage Colony Stimulating Factor (M-CSF), Platelet-Derived Endothelial Cell Growth Factor (PD-ECGF), and Stem Cell Factor (SCF), may promote the activation, proliferation, and/or stimulation of cell types involved in the wound healing process.

EGF is a polypeptide growth factor (the mature, processed form is 53 amino acids in length. In humans, this protein inhibits gastric acid secretion while murine EGF is known to be mitogenic for a number of cell types, including endothelial, epithelial, and fibroblastic cells.

FGF comprises a family of single chain proteins 14-18 kD in size which tightly bind the potent anticoagulant heparin. Two FGF types, acidic and basic, have been reported. The 146 amino acid basic form (bFGF) is more stable and ten times more potent in stimulating mesodermal cells, such as fibroblasts, endothelial cells, and keratinocytes, than acidic FGF (aFGF).

Insulin is a protein hormone secreted by the cells of the pancreatic islets. It is secreted in response to elevated blood levels of glucose, amino acids, fatty acids, and ketone bodies, promoting their efficient storage and use as cellular fuel by modulating the transport of metabolites and ions across cell membranes and by regulating various intracellular biosynthetic pathways. Insulin promotes the entry of glucose, fatty acids, and amino acids into cells. Additionally, it promotes glycogen, protein, and lipid synthesis while inhibiting glucogenesis, glycogen degradation, protein catabolism, and lipolysis. Insulin consists of $\alpha$ and $\beta$ subunits linked by two disulfide bridges.

IGF-I an IGF-II are members of a growth hormone-dependent family which mediate the effects of growth hormones. These proteins are known to be important in the regulation of skeletal growth. Both molecules have close structural homology to insulin and possess similar biological activities. IGF-I shares a 43% amino acid sequence homology with proinsulin, while IGF-II shares 60% homology with IGF-I. The IGFs are somewhat unique as compared to the other proteins described herein, in that there is essentially no detectable free IGF species present in the blood plasma of mammals. Instead, the IGFs are bound to specific carrier plasma proteins of higher molecular weight. Both IGF species stimulate DNA, RNA, and protein synthesis and are involved in the proliferation, differentiation, and chemotaxis of some cell types. Local administration of IGF-I is known to stimulate the regeneration of peripheral nerves. In addition, IGF-I and PDGF, when administered topically to wounds in pigs, synergize to promote more effective healing than when either factor is administered alone.

Interferons were first identified as proteins that render cells resistant to infection from a wide range of viruses. Three Interferon types have been identified, $\alpha$-IFN, $\beta$-IFN, and $\gamma$-IFN, which are produced by activated T and NK (natural killer) cells. $\alpha$-IFN is comprised of a family of 15 or so closely related proteins while $\beta$-IFN and $\gamma$-IFN exist as single species. In addition, a synthetic consensus $\alpha$-IFN, designed to incorporate regions of commonality among all known $\alpha$-IFN subtypes, is disclosed in U.S. Pat. No. 4,897,471, hereby incorporated by reference. All IFNs are growth inhibitory molecules playing an important role in the lymphokine cascade. Each exerts a wide range of regulatory actions in normal cells, cancer cells, and host immune defense cells. $\gamma$-IFN's activities include macrophage activation for enhanced phagocytosis and tumor killing capacity. At present, these proteins are mainly used in cancer therapy.

The Interleukins (ILs) are a polypeptide family playing a major role in the body's immune response. They are produced by many cell types, particularly T cells, in response to antigenic or mitogenic stimulation. IL-1 is produced following foreign antigen recognition. In addition to mediating the immune response IL-1 is involved in the inflammatory response to acute infection. IL-1 activates B cells and T cells. It induces IL-2 synthesis. It serves as a cofactor in B cell proliferation and differentiation. It enhances T cell and NK cell toxicity. IL-1 also enhances the response of bone marrow progenitors to various colony stimulating factors (CSFs). In inflammation, IL-1 causes bone marrow granulocyte release, serves as a polymononuclear cell chemoattractant, stimulates fibroblast proliferation, and plays a role in collagenase release.

T cell synthesis of IL-2 is induced by IL-1. IL-2 is a B cell and T cell growth factor. It is also a NK cell growth and activation signal, stimulating them to become highly cytotoxic lymphokine activated killer (LAK) cells. IL-2 also regulates macrophage activity, promoting cytotoxicity. IL-3, also called multi-CSF, synthesized by antigen or mitogen induced T lymphocytes, is involved in the growth and differentiation of hematopoietic progenitors. In vitro, IL-4 is essential for mucosal and connective tissue growth. It also enhances the tumoricidal activity and antigen presenting ability of macrophages. IL-4 synergistically interacts with CSFs on many non-terminally differentiated hematopoietic cell lineages. Further, it activates resting B cells. IL-4 also down regulates monocyte immune function, inhibiting monocyte and macrophage activity and suppressing IL-8 production in stimulated monocytes.

After antigenic stimulation, IL-5 induces B cell growth and differentiation into immunoglobulin secreting cells. It also stimulates the proliferation, differentiation, and activation of eosinophils. IL-6, produced by fibroblasts, endothelial cells, and monocytes, in addition to T cells, induces the terminal differentiation of activated B cells into antibody producing cells. Further, it activates hematopoietic progenitors to respond to IL-3. IL-7 induces in vitro B cell and thymocyte proliferation. IL-8 is expressed in both immune and non-immune cell types. In stimulated monocytes, IL-8 expression is suppressed by IL-4, while expression in fibroblasts and endothelial previously activated by tumor necrosis factor (TNF) or IL-1 is not suppressed by IL-4. In vivo, factors mediating neutrophil migration are unknown, but IL-8, having potent neutrophil activating and chemotactic activities, may mediate in vivo neutrophil accumulation.

IL-9 is expressed in certain T cell lines and by mitogen stimulated peripheral blood lymphocytes. IL-9 enhances mast cell proliferation and it also stimulates IL-6 production in bone marrow-derived mast cells. Recently discovered in mice, IL-10, also called mouse cytokine synthesis inhibitory factor (CSIF), inhibits cytokine production in stimulated non-humoral T cell populations.

KGF is an epithelial cell specific mitogen secreted by normal stromal fibroblasts. In vitro, it has been demonstrated to be as potent as EGF in stimulating the proliferation of human keratinocytes.

M-CSF, also known as CSF-1, is a homodimeric colony stimulating factor which acts solely on macrophage progenitors. This macrophage lineage specific protein is produced constitutively in vitro by fibroblasts and stromal cell lines. In vivo, unlike other CSFs, M-CSF appears early in embryogenesis, suggesting a potential developmental role for this polypeptide.

PD-ECGF is a platelet derived endothelial cell mitogen having a molecular weight of approximately 45 kD. In contrast to the FGF family of endothelial cell mitogens, PD-ECGF does not bind heparin nor does it induce fibroblast proliferation. However, PD-ECGF does stimulate endothelial cell growth and chemotaxis in vitro and angiogenesis in vivo.

PDGF is a potent stimulator of mesenchymal cell types, like fibroblasts and smooth muscle cells, but it does not stimulate the growth of epithelial or endothelial cells. At low concentrations, PDGF acts as a chemoattractant for fibroblasts, and also as a chemoattractant and activating signal for monocytes and neutrophils.

Recombinant SCF is a novel cellular growth factor which stimulates the growth of early hematopoietic progenitor cells, neural stem cells, and primordial germ stem cells. SCF exhibits potent synergistic activities in conjunction with colony stimulating factors, resulting in increased numbers of colonies and colonies of greater size. Thus, administration of SCF to mammals in pharmacologic doses, alone or in combination with other colony stimulating factors or other hematopoietic growth factors, may lead to the improvement of damaged cells in a number of divergent organ systems.

TGF-α and TGF-β act synergistically to induce anchorage independent growth in certain cancer cell lines. TGF-β is comprised of a class of disulfide linked homodimeric proteins, each chain being composed of 112 amino acids. This dimeric protein produces many biological effects, such as mitogenesis, growth inhibition, and differentiation induction depending upon the assay used. TGF-β1 is the most studied TGF-β species in relation to wound healing. As a class, TGF-β is a potent monocyte and fibroblast chemoattractant.

Because each of these recombinant growth factors mentioned above may be capable of acting as a mitogen, inhibitor, or chemoattractant for the cell types heavily involved in the wound healing process, i.e. monocyte/macrophage, neutrophil, fibroblast, and endothelial and epithelial cells, they may be used in the methods of the invention. EGF, has been found to accelerate the healing of surface wounds and burns when repeatedly applied to the wound site. PDGF and TGF-β increase the healing rate of incisional wounds when administered one time to the incision site shortly after the wound is made.

The soluble factors may be proteins or may be expressed in cells. Protein, peptide, or polypeptide refers to a polymer of amino acids, and these terms are used interchangeably. The polymer may include natural or unnatural amino acids. The protein or polypeptide may be produced in vitro or in vivo via natural, recombinant, synthetic, or other means. The protein or polypeptide may have post-translational modifications or may have been modified chemically to include phosphorylation, glycosylation, farnesylation, acetylation, methylation, oxidation of thiols, etc.

The term "cells" as used herein means a single unit biological organism that may be eukaryotic or prokaryotic. The eukaryotic cell family includes yeasts and animal cells, including mammalian and human cells. Cells that may be useful in conjunction with the present invention include cells that may be obtained from a patient, or a matched donor, or established cell lines. Cells may be isolated and extracted from the patient, and/or genetically reengineered to produce a host of cytokines, antibodies, or other growth factors to aid in the wound healing process.

Recombinant can refer to organisms, cells, nucleic acids, and proteins. Recombinant cells and organisms are cells and organisms containing recombinant DNA. Recombinant DNA refers to a nucleic acid sequence which is not normally found in nature. Usually this term refers to two or more pieces of DNA spliced together to form an unnatural product. Recombinant protein is protein produced from recombinant DNA (i.e., a nucleic acid which differs from that which occurs in nature). In producing a recombinant protein, the regulatory sequences of the gene encoding the protein are usually different than the ones that occur in the natural gene. The gene also may have been placed in an organism which normally does not possess the gene in order to produce that protein in the desired organism.

The insertion of desired genes or other nucleic acid constructs into cells seeded onto the new microfabricated membranes or into the new tissue analogs or substitutes can be accomplished using routine genetic and recombinant engineering techniques, e.g., as described in Ausubel et al., eds., 1989, *Current Protocols in Molecular Biology*, Green Publishing Associates, Inc. and John Wiley & Sons, Inc., New York.

As is the case with cell culture chamber 502a, one cell culture chamber may be connected to numerous microchambers 230 (including thousands or more). In some embodiments, one microchamber may be connected to several cell culture chambers. For example, microchamber 230' may receive soluble mediators from cell culture chambers 502b, 502c, and 502d. In this manner, several different mediators may be supplied to areas of the wound-facing surface.

In some embodiments, microfluidic pumps and/or valves may be used to transport and/or regulate the soluble mediators. For example, a microfluidic control line 506 may cross one or more microchannels to form a valve to control the flow of mediators to various microchambers. In some embodiments, complex networks of microfluidic valves, pumps and channels may be used to control the delivery of various soluble mediators to the microchambers. Various soluble mediators, such as PDGF, EGF, GM-CSF, FGF and other suitable mediators, may be used either alone or in combination.

Seeding of cell culture chamber 502a may be achieved by introducing a suspension of cells in a fluid medium to cell culture chamber 502a through a self-sealing port 510 or other suitable delivery mechanism. Port 510 may lead directly into cell culture chamber 502a, or be connected via a channel 512. In some embodiments, a main or central cell reservoir (not shown) may be used to initially store cells suspended in a liquid medium, and channels may lead from the main reservoir to several smaller cell culture chambers. Reagents similarly may be added directly to cell culture chambers via a port, or added to a main reservoir and then distributed to cell culture chambers. Conditions for supporting the viability of the cells may be maintained by providing nutrients, water, etc. by injecting media through port 510 or delivering these factors through a microchannel.

In some embodiments, instead of cell culture chambers, drug holding chambers may be included in the matrix of wound healing device. Drugs may be held in the chambers and released over time at a selected rate in a manner similar to the soluble mediators described above. Drugs potentially useful in the treatment of wounds include: antibiotics, silver; silver nitrate; mafenide acetate; povodine iodine; silver sulfadiazene; macrolides; penicillins; cephalosporins; aminoglycocides; and quinolones. Other drugs of use in wound healing include: angiogenic factors; vitamins; peptides; and genetic material.

Figure 5B:
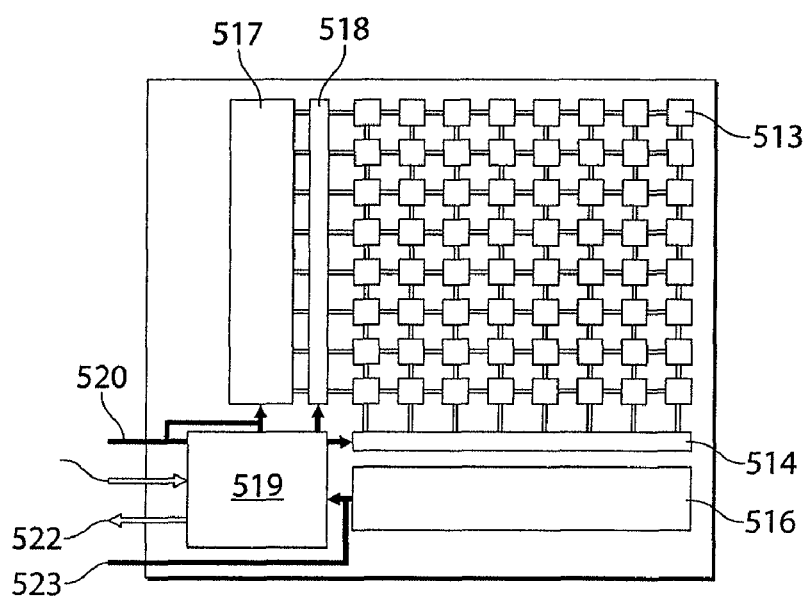
FIG. 5b is a top view of one embodiment of a wound therapy device including embedded cell culture chambers, row and column selection circuitry, processing circuitry, row and column decoding circuitry, drug reservoirs, biosensors, information and data buses, as well as fluid management buses.

In one embodiment, a feedback control system employing biosensors may be used as part of the wound healing process. A schematic representation of one example of a feedback control system embodiment is provided in FIG. 5b. Depending on the particular wound type, advantageous strains and rates of strains can be time-dependent, or even dependent on the state of healing. A mechanism which obtains data on the degree of healing or lack thereof in the wound may be helpful for adjusting operational parameters. A feedback system may be used in which biological or physical conditions and parameters are measured and used to determine vacuum pressures and locations, and/or to control wound healing mediator delivery and/or cell delivery. Examples of such conditions and parameters include changes that are directly responsible for wound healing such as cellular proliferation and the rate of neovascularization. Further examples of conditions or parameters which may be correlated with effective wound healing include, but are not limited to, the fluid content of the wound, wound color, height of the wound relative to surrounding tissue, and wound tissue compliance. Further examples of conditions or parameters that may be correlated with effective wound healing and may be used in a feedback system to improve the conditions in the wound healing microchambers include, but are not limited to: pH, dissolved oxygen content, hemoglobin concentration, hemoglobin oxygen saturation, bacterial count, concentration of toxins, concentration of metabolic substrates, and concentration of metabolic by-products. Any of these conditions or parameters listed may occur in combination and may be used to give an indication of effective wound healing.

The measured parameters that reflect the physical condition of the wound may be determined by a variety of transductions methods. The transduction methods include, but are not limited to those of: piezoelectric, piezoresistive, capacitive, resistive, inductive, pH, optical emission, optical transmission, optical transillumination, optical excitation/decay, and chemical. For example, a piezoresistive strain gauge mounted on the wound can include a mechanical method to detect the height of the wound relative to the surrounding tissue. This detection of relative wound height also may be detected via optical methods. Further, an optical device that can detect color changes or hemoglobin levels (due to new vessel growth) in the wound can serve to monitor the physical condition of the wound, as can other devices that can measure changes such as these. Biosensors may be distributed throughout the array of microchambers 513 or located at the periphery 514, 516 of the array.

The sensors may input data into a processing unit 519 that determines the rates of change of these parameters, or a single or multiple higher order mathematical functions base of these parameters. Based on the received data and the analyses performed by the processing unit, the control system may determine and effect the various levels for the operational parameters of either an individual microchamber, a group of microchambers, or the entirety of the microchambers in the wound healing device. This is realized via actuators either distributed throughout the array of microchambers 513 or located at the periphery 517, 518 of the array.

The control system may modify a variety of physical parameters in order to alter wound healing conditions in response to the measured condition(s). The modifiable parameters include, but are not limited to: vacuum pressure, positive pressure, tissue compression, tissue tension, pH, oxygen infusion rate, antibiotic infusion rate, drug infusion rates, chemotherapy infusion rates, medium infusion and extraction rates, infusion rates of soluble mediators, infusion rates of insoluble mediators, infusion rates of living and defunctionalized cells, infusion rates of proteins, and externally applied wound contraction stress. The control system also may serve to modulate flow in a single or multiple fluid intake channels 520 as well as modulate flow in a single or multiple fluid and waste outflow channels 523. Further data/information transfer buses 512, 522 may be provided as a component of the control system.

In one embodiment, the device is capable of distributing and depositing multiple, distinct layers of materials upon the wound bed. The deposition of distinct layers may be performed in order to construct in vivo multi-layer, biologically composite and laminates. These biological laminates are made of layers with varying thicknesses. The layers may be deposited in a combination of spatial and temporal patterns and sequences in order to optimize wound healing. For example, wound healing may be improved by the deposition of a relatively thick layer of a certain biologically active agent in one region of the wound and a relatively thin layer of the same material in another region of the wound. The materials that make up such a biological composite or laminate include but are not limited to: living cells, defunctionalized cells, extracellular matrix proteins, proteins, thermoplastic polymers, thermoset polymers, biodegradable polymer, soluble wound healing mediators, insoluble wound healing mediators, inorganic materials, and nanofabricated materials including nanoparticles and/or nanotubes. Deposition of these biocomposite materials serves to reconstitute the complex barrier function normally provided by the outer surface of an organ or organ system. In addition, this method includes the capacity to deposit parenchymal cells in order to reconstitute organ structure and function in a controlled manner. In the case of a skin wound, this method allows for deposition of a specific combination of materials, biological mediators, and cell types in order to recapitulate the structure and function of the dermis. The method then allows the deposition of a distinct combination of cell types in order to recapitulate the structure and function of the epidermis.

In one embodiment, an array of microchambers is capable of distributing and depositing multiple layers of materials upon substrates other than a wound in order to construct in vitro tissue explants and engineered tissues. This construction may be accomplished in a manner similar to that used in the creation of in vivo biocomposites as described above. In the case of the in vitro tissue explants and engineered tissues, the starting substrate is not a wound bed, but rather a biocompatible substrate.

Figure 6A:
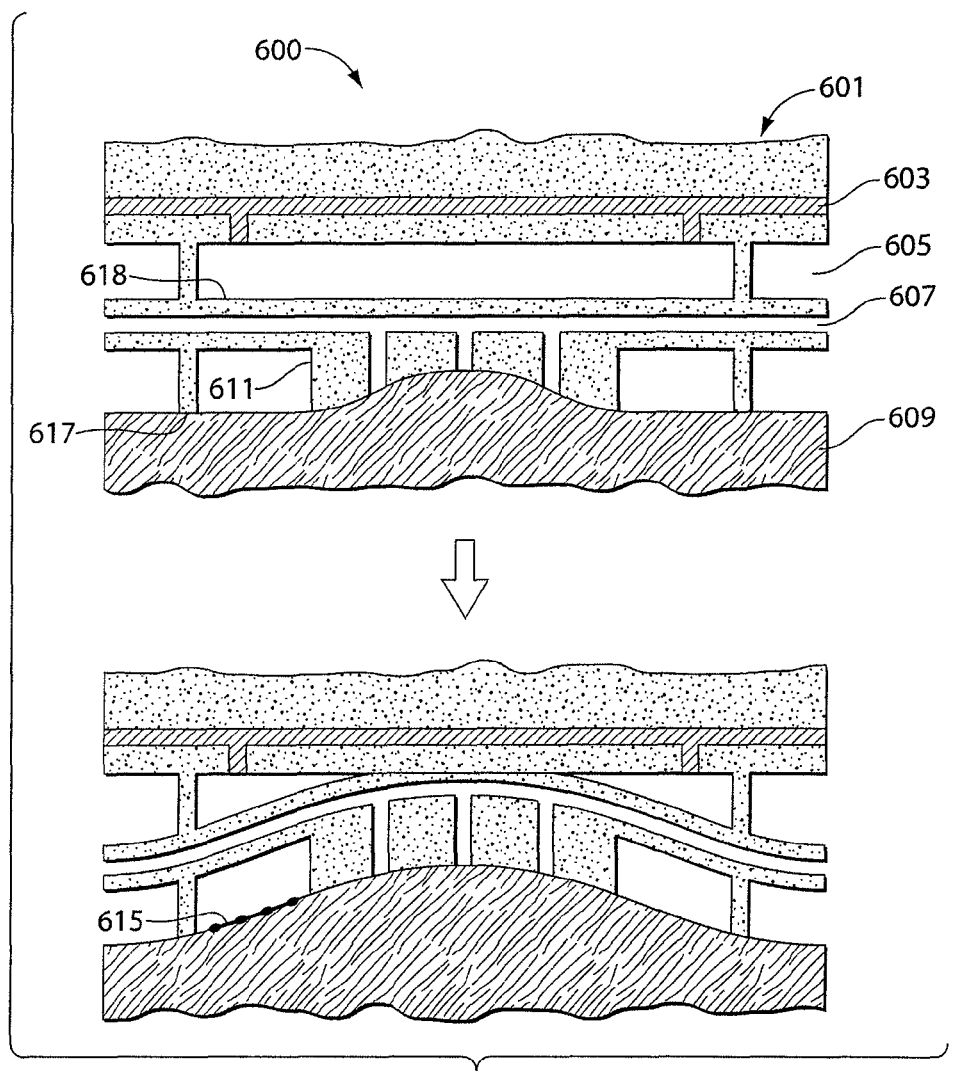
FIG. 6a shows a cross-sectional side view of one embodiment of an individual microchamber demonstrating an actuation scheme to apply micromechanical stimuli to a wound surface.

In one embodiment, a wound therapy device 601 is capable of applying relatively large mechanical strain in underlying wound tissue through the induction of relatively large displacements via active mechanical elements within the microchambers. In FIG. 6a, a microchamber 600 contains a face-plate 611 that enables the application of vacuum pressure to tissue 609 underlying a microchamber, thereby anchoring the wound tissue relative to the face-plate 611. Other means of anchoring the tissue to the face plate include, but are not limited to: microfabricated anchoring posts, microfabricated anchoring ridges, and adherent surface textures. This face-plate may be separated from an overlying vacuum chamber by a deformable diaphragm 618. In one method associated with this embodiment, the tissue may be first immobilized relative to the face-plate with the application of a vacuum pressure via embedded microchannels 607. A relatively large strain 615 then may be induced in the tissue of the wound bed when a second, smaller amplitude vacuum pressure is applied to the overlying vacuum chamber. Applying the vacuum to the overlying vacuum chamber causes the diaphragm to deform and the tissue to move vertically relative to the tissue that is anchored at the edge of the microchamber. Anchoring of the tissue at the edge of the microchamber may be realized through various methods including, but not limited to: the application of vacuum pressure, microfabricated anchoring posts and ridges, and adherent surface textures. Using such a construct, the induction of deformations in the range of 1 to 1000 microns is possible.

Figure 6B:
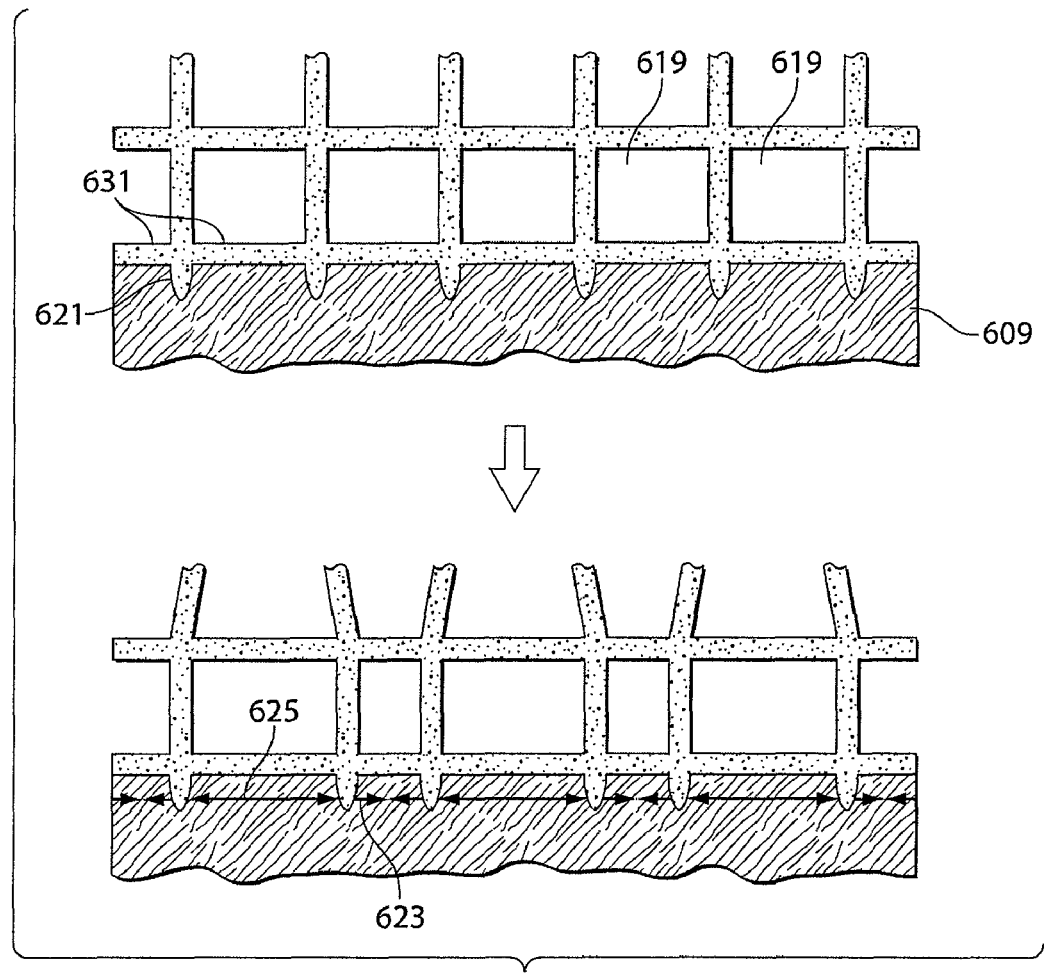
FIG. 6b shows a cross-sectional side view of an alternative embodiment of microchambers demonstrating an actuation scheme to apply micromechanical stimuli to a wound surface.

In FIG. 6b the microchambers are shown to be separated from an overlying chamber 619 by a deformable membrane 631. Chamber 619 is configured such that it produces lateral compression 623 of the wound therapy device when a vacuum pressure is applied to the chamber and produces a lateral elongation 625 when a positive pressure is applied to the chamber.

In one method associated with this embodiment, the tissue first may be immobilized relative to the face-plate with the application of a vacuum pressure. A relatively large strain is then induced in the tissue of the wound bed when a second vacuum pressure is applied to every other chamber and the remaining chambers are supplied with a positive pressure. Applying the spatially alternating vacuum pressure and positive pressure to the overlying vacuum chambers causes the chambers to collapse and expand respectively. This collapse and expansion causes the wound tissue to move vertically relative to the adjacent tissue thereby inducing physically localized regions of relative tissue compression and tissue tension. The tissue deformation at the edge of each microchamber may be realized through various methods including, but not limited to: the application of vacuum pressure, microfabricated anchoring posts and ridges, and adherent surface textures. Using such a construct, in some embodiments, the induction of deformations in the range of 1 to 1000 microns is possible.

Figure 6C:
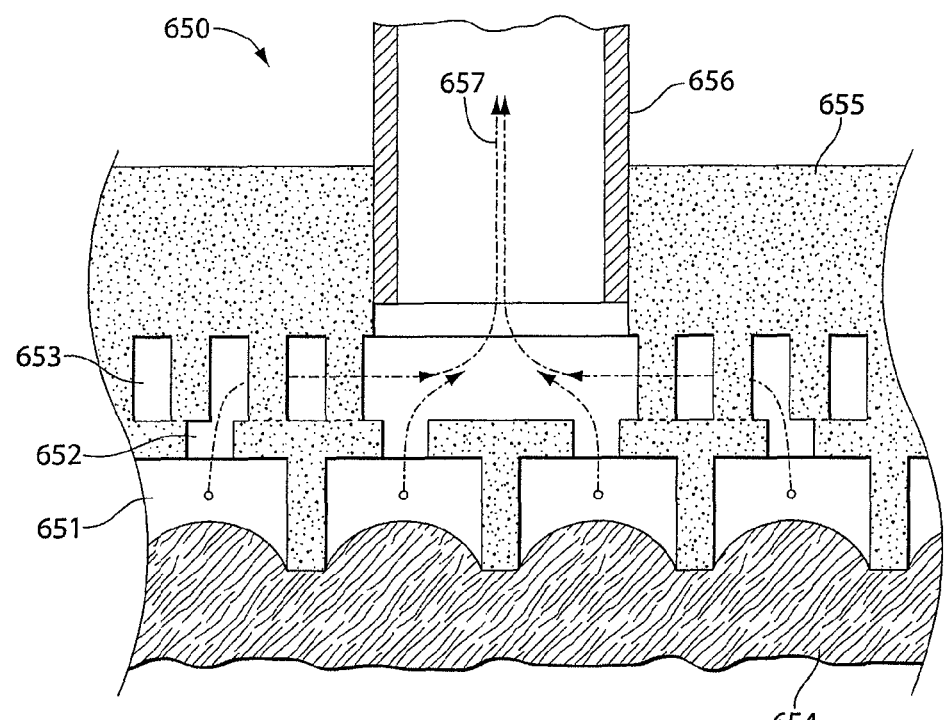
FIG. 6c shows a cross-sectional side view of a portion of one embodiment of an apparatus for promoting tissue growth.

One embodiment of an apparatus 650 configured to permit removal of materials from a wound surface 654 (or other tissue surface) is illustrated in FIG. 6c. Apparatus 650 includes a substrate 655 with a plurality of microchambers 651. Each microchamber 651 includes a fenestration 652 through which material can be removed from microchambers 651. Additionally, fenestration 652 allows for the transmission of vacuum pressure to microchamber 651. A vacuum pressure may be applied to the microchamber through interface tubing 656 and via a vacuum distribution layer 653. Distribution tubing 656 also may be used for transporting materials away from microchambers 651. Arrow 657 shows a path for evacuated materials through interface tubing 656.

Figure 7:
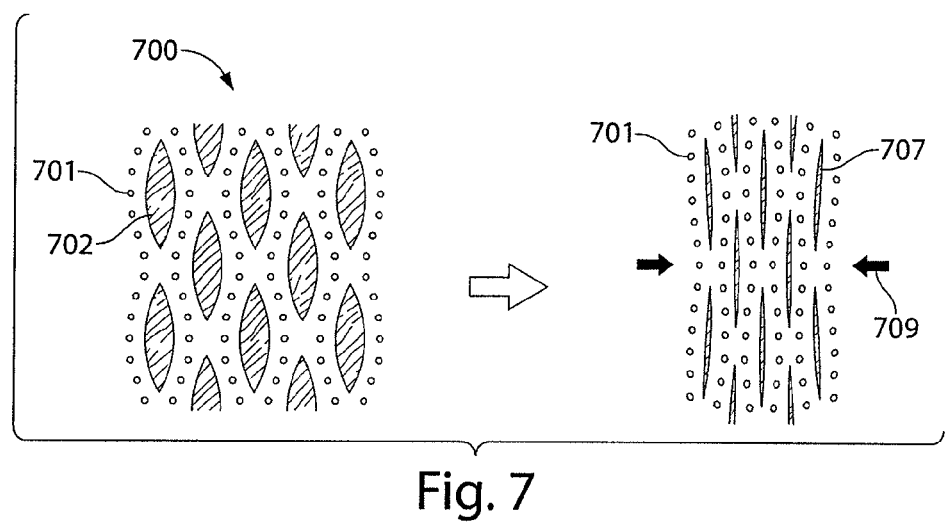
FIG. 7 shows a plan view of one embodiment of microchambers constructed and arranged to apply macroscopic contraction tension to a wound surface via collapsible chambers embedded within the device.

In one embodiment, the device is capable of applying macroscopic external compressive stress to the wound in order to enhance and/or optimize wound contraction. As shown in FIG. 7, the wound therapy device is outfitted with embedded mechanical actuators that enable mechanical contraction of the wound therapy device itself. In one embodiment, collapsible chambers or regions of relatively compressible materials 701 are embedded throughout the bulk of the device. On the surface of the device the areas underlying the chambers or compressible regions are surrounded by areas of the device surface that are strongly adherent to the wound surface 702. This strong adherence may be realized through various methods including, but not limited to: the application of vacuum pressure, microfabricated anchoring posts and ridges, and adherent surface textures. The region of the wound healing device surface underlying the collapsible chambers or regions of relatively compressible material are non-adherent or are relatively less adherent. By activating a series of localized mechanical actuators in or near the collapsible chambers or regions of relatively compressible material, two spatially separated regions of wound tissue that are strongly adherent to the surface of the device may be brought into close proximity 707. This action causes a macroscopic compression of the underlying wound bed 709 while a micromechanical stimulus continues to be delivered to the tissue of the wound bed. By applying this macroscopic compression while continuing the application of microscopic mechanical stimuli, effective wound healing is enhanced. In some embodiments, a wound may be contracted by at least 10% by area, and in some embodiments, up to 90% by area.

One mode of realizing localized mechanical actuation in or near the collapsible chambers or regions of relatively compressible material is the application of relative vacuum to the chambers or regions. Other modes of realizing localized mechanical actuation include, but are not limited to: piezoelectric forces, electrostatic forces, magnetic forces, thermal expansion/contraction forces, chemical expansion/contraction forces, hydraulic forces and pneumatic forces. In some embodiments, one or more non-mechanical tissue stimuli may be employed, for example, thermal, electrical, ionic, ultrasonic, radiofrequency, photonic, chemical and optical stimuli.

In some embodiments, an apparatus including a plurality of microchambers may be affixed to and/or integrated into the surfaces of medical devices. The medical devices to which the microchamber array is applied may be manufactured in such a way that the microchambers are integrated into the device such that the manufacturing process for the device includes the fabrication of the microchambers. In alternative embodiments, a pre-fabricated form of the microchamber array may be applied to one or more surfaces of an independently manufactured device. Medical devices that may incorporate the microchambers include, but are not limited to: urinary catheters; cardiac catheters; pulmonary arterial catheters; endoscopes; bronchoscopes; implanted medical electronics; gastrostomy tubes; jejunostomy tubes; colostomy tubes; ventriculoperitoneal shunts; orthopedic hardware; and spine surgery hardware.

In some embodiments, the microchambers and other features may be constructed of a variety of materials including, but not limited to: metals; ceramic; polymers; and living tissue.

In some embodiments, an apparatus employing microchambers may be deployed to manage active hemorrhage. In such embodiments, a microfluidic network may be used to infuse pro-coagulant materials into specified microchambers. Other selected microchambers may perform alternative functions, such as evacuating clotted and unclotted blood. Through use of integrated compression chambers of baffles, the microchamber array also may provide hemostasis via direct compression of the bleeding tissue and or organ.

In some embodiments, an apparatus including microchambers may be deployed as a primary mode of providing chemotherapy in cancer patients. In such embodiments, a microfluidic network may be used to infuse chemotherapy or brachytherapy materials into specified microchambers that are positioned adjacent to a tumor. Other selected microchambers may perform alternative functions, such as applying suction to the tumor to ensure close approximation of the therapeutic materials.

In some embodiments, an apparatus including microchambers may be used in the treatment burn wounds. In such embodiments, a microfluidic network may be used to infuse antibiotics and cells onto the surface of the wound. Other selected microchambers may perform alternative functions, such as evacuating blood and applying suction to the wound to ensure dressing adherence. In such embodiments, the microchambers may be used to instill cells, such as keratinocytes or other skin cells, for example, onto the wound surface in a concerted manner in order to reconstitute the dermis and epidermis in part or in whole. In such embodiments, several different tissues, materials, and living cells may be instilled in order to reconstitute the structure and/or function of the dermis and/or epidermis.

In some embodiments, an apparatus including microchambers may be deployed for the management of open abdominal wounds. Open abdominal wounds occur when swelling of the abdominal organs prevents the fascial layers of the abdomen from being reapproximated. Abdominal wounds also may be left open intentionally in certain scenarios in order to provide surgeons with the capacity to serially evaluate organs or abdominal regions of concern without the need to re-open the abdomen. This situation occurs frequently in abdominal trauma scenarios where active hemorrhage is controlled via laparotomy and packing of the abdomen with sponges. In this case, extensive efforts to arrest the bleeding are not made in lieu of temporarily closing the wound with a Bogeta bag—a clear, sterile plastic sheet. In this case the abdomen is re-evaluated by removing the plastic sheet at a specified interval in time. In some embodiments, an apparatus including microchambers may be used to replace the clear, sterile plastic sheet.

In some embodiments, an apparatus including microchambers may be used as patch for repair of structural defects in the body such as hernias. In such embodiments, the apparatus may be sutured in place to provide a mechanically robust repair of the hernia. In another embodiment, the distributed suction at the level of the microchambers may serves as a method of affixing the repair patch in place. Hernias that may be repaired using a patch integrated with apparatuses disclosed herein include, but are not limited to: inguinal hernias; ventral hernias; incisional hernias; congenital diaphragmatic hernias; and traumatic hernias. In some embodiments, antibiotics may be infused through channels (such as microchannels) to the microchambers in order to treat and/or prevent infection. The patch may be made up partially or entirely of resorbable materials.

In some embodiments, an apparatus including microchambers may be used in minimally invasive surgery such as: endoscopy; laparoscopy; thoracoscopy; cystoscopy; and arthroscopy. In such embodiments, the apparatus may be rolled up into a tube configuration and inserted into the body of cavity under exploration. The diameter of the rolled microchamber apparatus may be less than that of the one or more trochar being used to access the body cavity.

According to another aspect of the invention, microstructures may be used to induce mechanical stimulation of tissue without connection to an controllable external source of pressure or force. That is, in some embodiments, microstructures themselves may provide stimulation of tissue by virtue of their shape and the force of being contacted to a tissue surface. In some embodiments, an area of protruding microstructures on a substrate may be contacted against a target tissue area, such as wound, by adhering the substrate to a subject in an area around the target tissue area. For example, in some embodiments, the substrate may resemble a typical adhesive bandage in that an adhesive area may hold a wound-facing surface against a wound.

In other embodiments, a controllable force (such as a vacuum applied to microchambers interspersed among the protruding microstructures) may be used to press protruding microstructures against the target tissue.

When two bodies come into contact, a contact stress profile is generated at the interface, and this contact stress profile typically is triaxial. The stress profile contains one axis of normal stress that is positioned perpendicular to the contact interface. In addition, the stress profile contains two axes of shear stress, both positioned parallel to the contact interface. This triaxial contact stress profile is transmitted to the bulk material of both bodies in contact. As it is transmitted, the stress produces deformation, or strain profiles in both of the bodies in contact. In the case where both surfaces in contact are smooth, the contact stress profiles are similarly smooth and continuous.

If one of the surfaces is patterned with protruding microstructures, the microstructures form localized increases in the contact stress profiles. This process of locally increasing the magnitude of stress due to microstructures interposed at a contact interface is known as stress concentration. By locally increasing the magnitude of the applied stress, the resulting local strain is increased, thereby increasing the mechanical stimulus for wound healing or otherwise promoting tissue growth. Protruding microstructures may be one or more of a variety of shapes. In some embodiments, the microstructures may be pillars, posts, or nibs. In some embodiments, the protruding microstructure may include mesas, recesses, pyramids, hemispheres, multi-tiered patterns, or any other suitable shape. In some embodiments, a protruding microstructure has a length, width and a depth, the depth being the perpendicular distance from the substrate base to the point of the microstructure that protrudes furthest from the substrate base. For purposes herein, the length and the width of the protruding microstructure are perpendicular dimensions that are also perpendicular to the depth. The larger dimension of the dimensions perpendicular to the dept is considered to be the length. In some embodiments, the ratio of the length to the width does not exceed one hundred. In some embodiments, the ratio of the length to the width does not exceed fifty, and in still further embodiments, the ratio of the length to the width does not exceed ten. In some embodiments, the length and width are essentially equal.

Figure 8A:
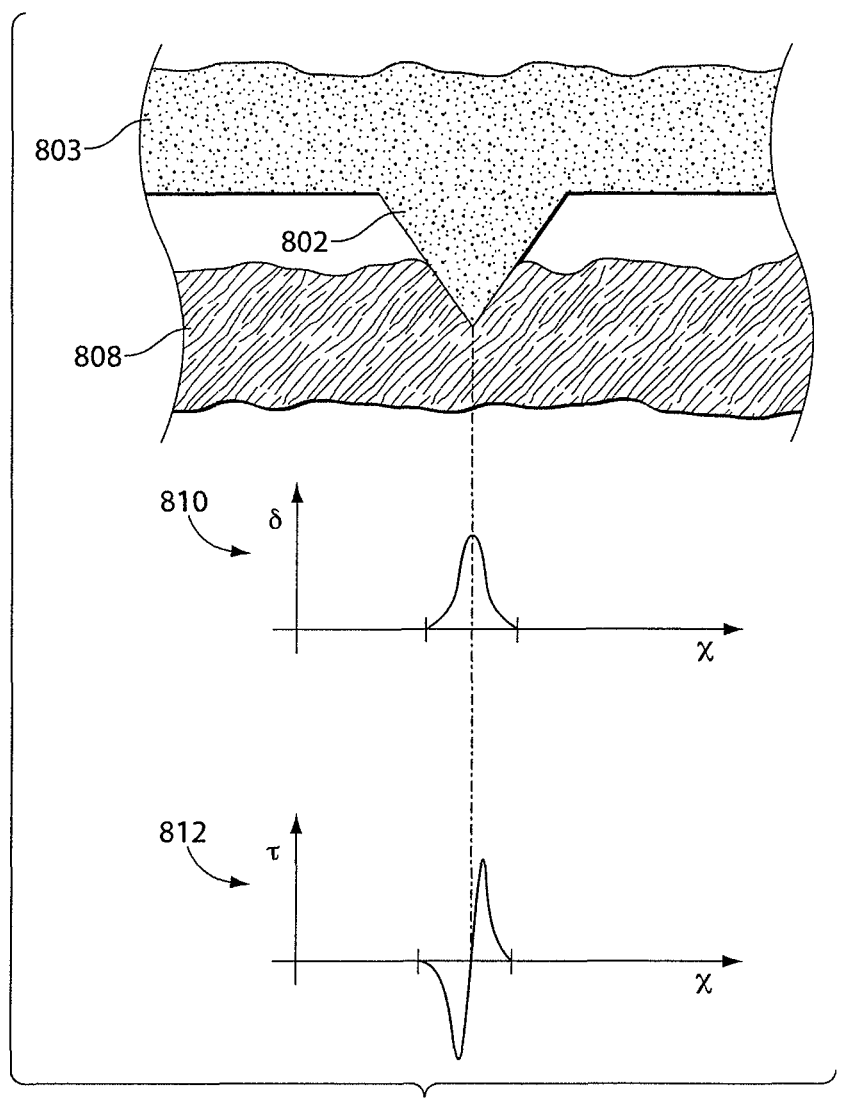
FIGS. 8a-8c show protruding microstructures according to further embodiments of the invention.
Figure 8B:
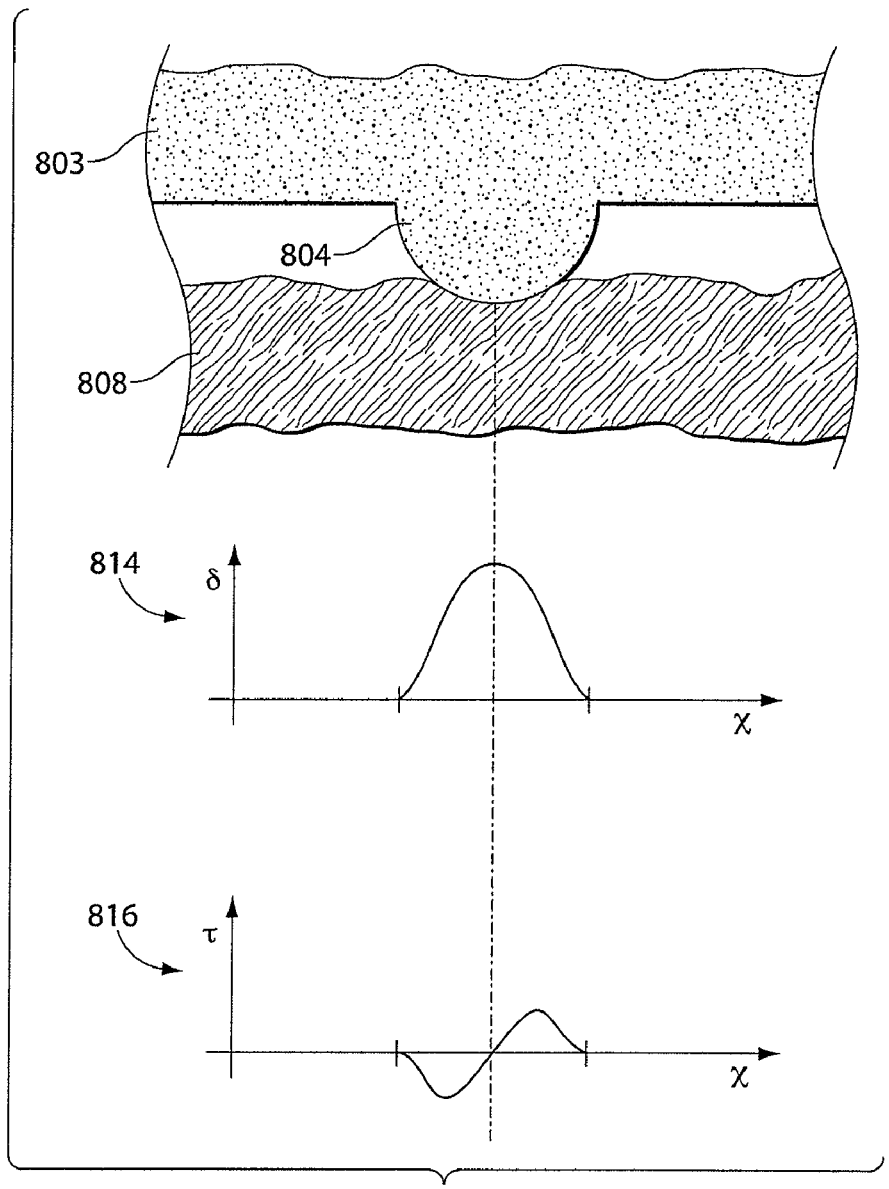
Figure 8C:
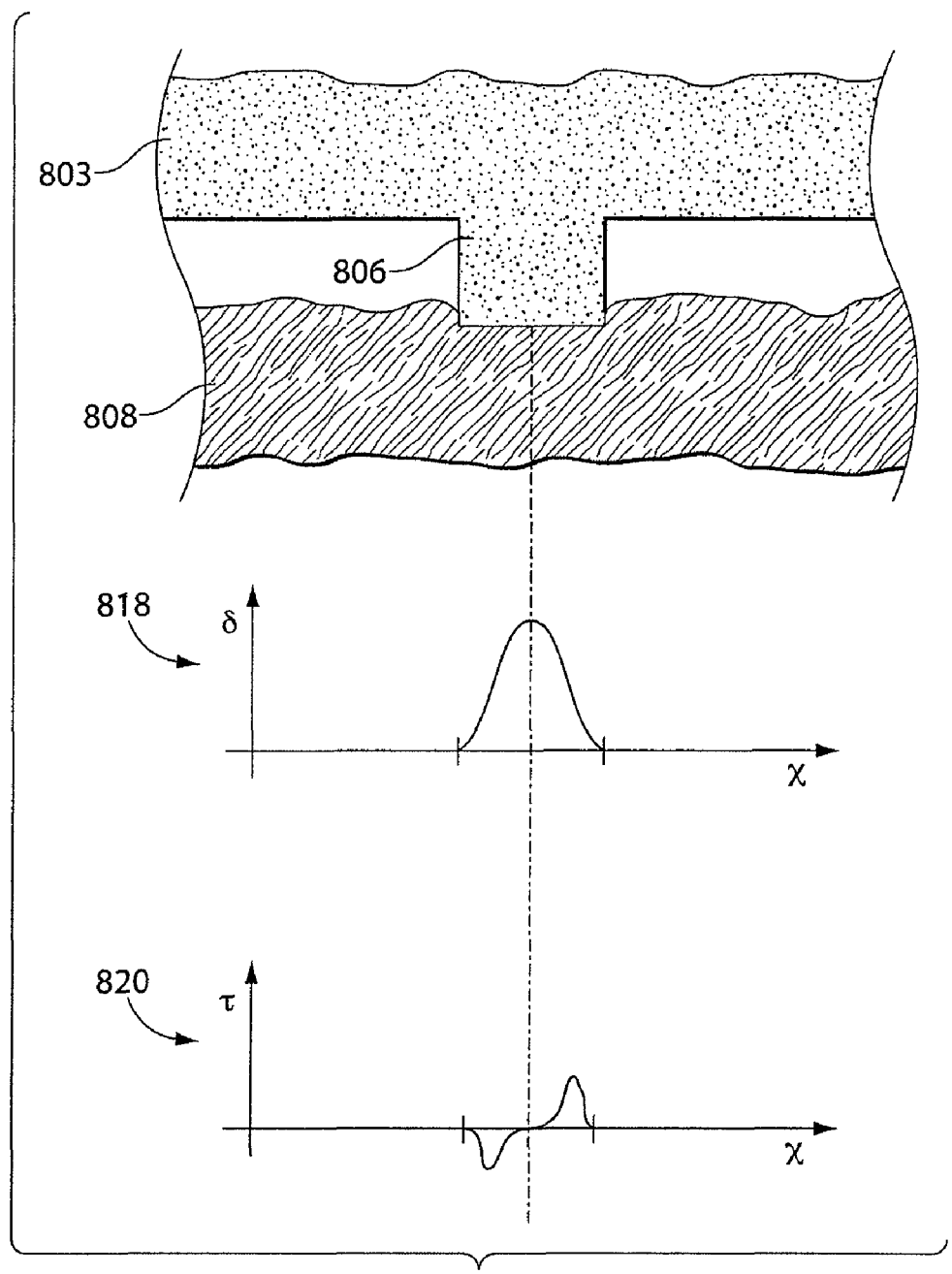

Each of FIGS. 8a-8c each shows and embodiment of a protruding microstructure contacting a tissue surface, and also corresponding predicted normal stress profiles and shear stress profiles.

FIG. 8a is a cross-sectional side view of a conical protruding microstructure 802 contacting a tissue surface 808. Conical protruding microstructure 802 protrudes from an apparatus substrate 803. Normal stress profile 810 shows the predicted normal stress that would be induced in tissue surface 808 along the x-direction, and shear stress profile 812 shows the predicted shear stress that would be induced in tissue surface 808 along the x-direction.

FIG. 8b is a cross-sectional side view of a hemispherical protruding microstructure 804 contacting a tissue surface 808. Hemispherical protruding microstructure 804 protrudes from a substrate 803. Normal stress profile 814 shows the predicted normal stress that would be induced in tissue surface 808 along the x-direction, and shear stress profile 816 shows the predicted shear stress that would be induced in tissue surface 808 along the x-direction.

FIG. 8c is a cross-sectional side view of a post protruding microstructure 806 contacting a tissue surface 808. Post protruding microstructure 806 protrudes from a substrate 803. Normal stress profile 818 shows the predicted normal stress that would be induced in tissue surface 808 along the x-direction. Shear stress profile 820 shows the predicted shear stress that would be induced in tissue surface 808 along the x-direction. Post protruding microstructure 806 may be cylindrical in a cross-section perpendicular to its depth, or post protruding microstructure 806 may be square in cross-section, or have any other suitable shape in cross-section.

Figure 9:
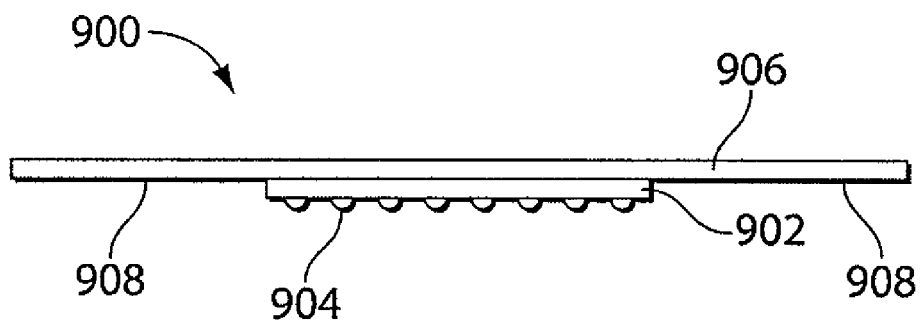
FIG. 9 shows a side view of an apparatus including protruding microstructures.

FIG. 9 illustrates one embodiment of an apparatus 900 resembles a typical adhesive bandage. A substrate 902 is provided with a plurality (for example, 10,000) of protruding microstructures 904 (not drawn to scale). Substrate 902 is attached to a backing 906, and backing 906 includes areas 908 having adhesive material for attachment to a subject. The force of the attachment to the subject presses microstructures 904 onto a wound surface or other tissue surface, resulting in tissue deformation.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. An apparatus for promoting tissue growth comprising:
a biocompatible matrix having a plurality of microstructures, each microstructure being constructed and arranged to apply a mechanical stimulus to a tissue surface, wherein the apparatus is configured such that an application of a first mechanical stimulus by a first microstructure of the plurality of microstructures is separately controllable from an application of a second mechanical stimulus by a second microstructure of the plurality of microstructures; and
a chamber which is controllable via pneumatic actuation to effect macroscopic contraction of a tissue wound; wherein
the chamber is compressible via pneumatic actuation such that when the biocompatible matrix is applied to the tissue wound and the chamber is compressed, at least two spatially separated regions of wound tissue are brought closer to each other.

2. An apparatus as in claim 1, wherein the first and second microstructures comprise microchambers which are constructed and arranged to apply a pressure to the tissue surface.

3. An apparatus as in claim 2, wherein the first and second microstructures comprise microchambers which are constructed and arranged to apply a vacuum pressure to the tissue surface.

4. An apparatus as in claim 3, further comprising a vacuum source fluidically connected to the microchambers via channels.

5. An apparatus as in claim 2, further comprising a pressure source fluidically connected to the microchambers to controllably apply pressures to the microchambers, wherein the pressures that are applied to the microchambers are controllable with microfluidic valves which are embedded within the apparatus.

6. An apparatus as in claim 1, wherein the application of the first mechanical stimulus by the first microstructure is controllable to vary the magnitude of the first mechanical stimulus without altering the magnitude of the second mechanical stimulus applied by the second microstructure.

7. An apparatus as in claim 1, wherein the matrix comprises silicone rubber, and each microstructure comprises a microchamber having a width of no more than 10 microns.

8. An apparatus as in claim 1, wherein the matrix comprises a multiplicity of microchambers constructed and arranged to apply a pressure to the tissue surface, each of the microchambers having a width of 10,000 microns or less.

9. An apparatus as in claim 1, further comprising:
a control system; and
a sensor to sense a tissue condition and provide information to a control system; wherein
the control system controls the application of the first mechanical stimulus by the first microstructure and the application of the second mechanical stimulus by the second microstructure based at least in part on the information received from the sensor.

10. An apparatus as in claim 1, wherein the microstructures are constructed and arranged to apply a mechanical stimulus to a tissue surface using at least one of: piezoelectric forces, electrostatic forces, magnetic forces, thermal expansion or contraction forces, and chemical expansion or contraction forces.

11. An apparatus as in claim 1, wherein the microstructures are controllable to effect macroscopic contraction of the tissue wound.

12. An apparatus as in claim 11, wherein the microstructures are controllable to effect a macroscopic contraction of a tissue wound by at least 10% and less than 90% in area.

13. An apparatus as in claim 1, further comprising:
a first channel;

a first group of microchambers of the plurality of microstructures, each of the microchambers of the first group being fluidically connected to the first channel;
a second channel different from the first channel; and
a second group of microchambers of the plurality of microstructures, each of the microchambers of the second group being fluidically connected to the second channel; wherein:
the application of the first mechanical stimulus by the first microstructure comprises the application of mechanical stimuli by each of the microchambers of the first group;
the application of the second mechanical stimulus by the second microstructure comprises the application of mechanical stimuli by each of the microchambers of the second group; and
the apparatus is configured such that is the application of mechanical stimuli by each of the microchambers of the first group is separately controllable from the application of mechanical stimuli by each of the microchambers of the second group.

14. An apparatus as in claim 1, wherein the plurality of microstructures includes a plurality of microchambers constructed and arranged to effect macroscopic contraction of the tissue, and wherein the first microstructure comprises the chamber.

15. An apparatus as in claim 14, wherein the matrix is adherable to the at least two spatially separated regions of wound tissue via vacuum pressure.

16. An apparatus as in claim 1, wherein the chamber overlies the first microstructure.

17. An apparatus as in claim 1, wherein the matrix is adherable to the at least two spatially separated regions of wound tissue.

18. An apparatus as in claim 17, wherein the matrix is adherable to the at least two spatially separated regions of wound tissue via vacuum pressure.

* * * * *